(12) United States Patent
Burak et al.

(10) Patent No.: US 9,409,896 B2
(45) Date of Patent: Aug. 9, 2016

(54) SUSTAINED RELEASE PHARMACEUTICAL COMPOSITIONS COMPRISING AN ANTIBACTERIAL AGENT

(75) Inventors: Eric S. Burak, East Haddam, CT (US); Danping Li, Middlebury, CT (US); David S. Dresback, Stonington, CT (US)

(73) Assignee: Melinta Therapeutics, Inc., New Haven, CT (US)

( * ) Notice: Subject to any disclaimer, the term of this patent is extended or adjusted under 35 U.S.C. 154(b) by 0 days.

(21) Appl. No.: 13/882,698

(22) PCT Filed: Nov. 1, 2011

(86) PCT No.: PCT/US2011/058743
§ 371 (c)(1),
(2), (4) Date: Dec. 16, 2013

(87) PCT Pub. No.: WO2012/061360
PCT Pub. Date: May 10, 2012

(65) Prior Publication Data
US 2014/0094463 A1    Apr. 3, 2014

Related U.S. Application Data

(60) Provisional application No. 61/408,830, filed on Nov. 1, 2010.

(51) Int. Cl.
*A61K 9/20* (2006.01)
*C07D 413/12* (2006.01)
(Continued)

(52) U.S. Cl.
CPC .............. *C07D 413/12* (2013.01); *A61K 9/205* (2013.01); *A61K 9/2018* (2013.01); *A61K 9/2054* (2013.01); *A61K 9/2059* (2013.01); *A61K 9/4858* (2013.01); *A61K 9/4866* (2013.01); *A61K 31/4192* (2013.01); *A61K 31/421* (2013.01); *A61K 31/5375* (2013.01); *A61K 47/14* (2013.01); *A61K 47/22* (2013.01); *C07D 263/22* (2013.01); *C07D 413/14* (2013.01)

(58) Field of Classification Search
None
See application file for complete search history.

(56) References Cited

U.S. PATENT DOCUMENTS 6,696,426 B2 *  2/2004  Singh et al. ............. 514/58
6,969,726 B2    11/2005  Lou et al.
(Continued)

FOREIGN PATENT DOCUMENTS

CN    1207895 A    2/1999
CN    1832932 A    9/2006
(Continued)

OTHER PUBLICATIONS

Gelucires: Pharmceutical Application, The major problems affecting design of any dosage form are related with the solubility and stabiity of drug substances, Aug. 27, 2008.*
(Continued)

*Primary Examiner* — Robert A Wax
*Assistant Examiner* — Melissa Mercier
(74) *Attorney, Agent, or Firm* — Wilmer Cutler Pickering Hale and Dorr LLP

(57) ABSTRACT

The present invention relates to carrier systems useful for pharmaceutical compositions. These carriers comprise an emulsifier, and also in further embodiments a polymeric dissolution aid. These carriers are useful for delivering pharmaceutical actives such as antimicrobial agents.

15 Claims, 4 Drawing Sheets

(51) Int. Cl.

| | | |
|---|---|---|
| *A61K 9/48* | (2006.01) | |
| *A61K 31/4192* | (2006.01) | |
| *A61K 31/421* | (2006.01) | |
| *A61K 31/5375* | (2006.01) | |
| *A61K 47/14* | (2006.01) | |
| *A61K 47/22* | (2006.01) | |
| *C07D 263/22* | (2006.01) | |
| *C07D 413/14* | (2006.01) | |

(56) References Cited

U.S. PATENT DOCUMENTS

| | | | |
|---|---|---|---|
| 7,527,807 B2 * | 5/2009 | Choi et al. | 424/488 |
| 8,968,781 B2 * | 3/2015 | Gowan et al. | 424/480 |
| 2002/0119196 A1 | 8/2002 | Parikh et al. | |
| 2003/0077297 A1 | 4/2003 | Chen et al. | |
| 2007/0208069 A1 | 9/2007 | Krishnan et al. | |
| 2009/0061009 A1 | 3/2009 | Schwarz et al. | |
| 2010/0234288 A1 * | 9/2010 | Jain et al. | 514/12 |

FOREIGN PATENT DOCUMENTS

| | | |
|---|---|---|
| GB | 2331458 A | 5/1999 |
| JP | 2000509720 A | 8/2000 |
| JP | 2001520984 A | 11/2001 |
| KR | 10-1999-0080453 A | 11/1999 |
| KR | 10-2005-0104152 A | 11/2005 |
| KR | 10-2006-0085686 A | 7/2006 |
| WO | WO98/07429 | 2/1998 |
| WO | WO99/21534 | 5/1999 |
| WO | WO 03/004001 A1 | 1/2003 |
| WO | WO-03/004001 A1 | 1/2003 |
| WO | WO-2005/058886 A1 | 6/2005 |
| WO | WO-2006118948 A2 | 11/2006 |
| WO | WO-2006-133397 A2 | 12/2006 |
| WO | WO-2006/133397 A2 | 12/2006 |
| WO | WO2008/085913 | 7/2008 |

OTHER PUBLICATIONS

Lancet, Oxazolidinone antibiotics, Dec. 2001.*
Gelucires:Pharmaceutical Application, The major problems affecting design of any dosage form are related with the solubility and stability of drug substances, Aug. 27, 2008.*
Bozdogan et al. (Oxazolidinones: activity, mode of action, and mechanism of resistance, International Journal of Antimicrobial Agents 23 (2004) 113-119).*
Chang et al. "Review of Current Issues in Pharmaceutical Excipients." *Pharm. Tech.* 31.5(2007):56-66.
Ho et al. "Effect of Topical Cyclosporine Rinse on Oral Lichen Planus." *N. Engl. J. Med.* 325.6(1991):435.
Jachowicz. "Dissolution Rates of Partially Water-Soluble Drugs from Solid Dispersion Systems. I. Prednisolone." *Int. J. Pharmaceutics.* 35.1-2(1987):1-5.
Park, J. et al. Physical properties of Gelucire-based sold dispersions containing lacidipine and release profiles. J. Kor. Pharm. Sci. Feb. 2010, vol. 40, No. 1, p. 9-14.
Australian Examination Report issued in corresponding to Australian Application No. 2011323594, dated Dec. 16, 2015, 4 pages.
S. Lemaire, et al. "Cellular Pharmacokinetics of the Novel Biaryloxazolidinone Radezolid in Phagocytic Cells: Studies with Macrophages and Polymorphonuclear Neutrophils", Antimicrobial Agents and Chemotherapy, vol. 54, No. 6, Jun. 2010, pp. 2540-2548.
Second Office Action and Search Report issued Jun. 10, 2015, in corresponding CN Application No. 201180063510.8 (English Translation).

* cited by examiner

| | Formula A | Formula C | Relative BE A / C |
|---|---|---|---|
| Cmax (ng/mL) | 3652.6 | 2593.6 | 1.4 |
| Tmax (hr) | 1.7 | 2.7 | 0.6 |
| T1/2 (hr) | 7.7 | 4.7 | 1.6 |
| AUC(0-inf) (ng*h/mL) | 31481.0 | 18107.6 | 1.7 |

SUSTAINED RELEASE PHARMACEUTICAL COMPOSITIONS COMPRISING AN ANTIBACTERIAL AGENT

RELATED APPLICATIONS

This application is a national stage application, filed under 35 U.S.C. §371, of International Application No. PCT/US2011/058743 filed Nov. 1, 2011, and claims priority to, and the benefit of, U.S. Provisional Application No. 61/408,830 filed Nov. 1, 2010, the contents of which are incorporated herein by reference in their entirety.

FIELD OF THE INVENTION

The present invention relates to carrier systems useful for pharmaceutical compositions. These carriers comprise an emulsifier. In further embodiments, these carriers also comprise a polymeric dissolution aid. These carriers are useful for delivering pharmaceutical actives such as antimicrobial agents. The present invention also relates to pharmaceutical compositions comprising an antimicrobial agent, methods for making pharmaceutical compositions, and to methods for treating, preventing, or reducing the risk of microbial infections.

BACKGROUND

An appropriate pharmaceutical carrier system is generally a requirement for the safe and effective delivery of a pharmaceutical active. The entire pharmaceutical composition, i.e. the pharmaceutical drug active formulated in a pharmaceutical carrier, can affect the bioavailability and also the pharmacokinetics and pharmacodynamics of the active. It is therefore important that a pharmaceutical composition be carefully developed and manufactured to deliver the desired pharmaceutical active in a safe and effective manner.

The delivery of antimicrobial agents for treating microbial infections can present special challenges. To provide therapeutic efficacy, it is generally desired that the antimicrobial agent be administered to the patient to achieve systemic concentrations in the bloodstream or target organs above a minimum inhibitory concentration (i.e. the MIC) and for a sufficient time against the particular microbial organism or organisms being targeted. Consequently, an antimicrobial agent that otherwise exhibits an effective antimicrobial profile in vitro can be ineffective, or even harmful, unless properly formulated for in vivo administration.

Therefore, the development and manufacture of suitable pharmaceutical carrier systems and pharmaceutical compositions for the safe and effective delivery of pharmaceutical drug actives, in particular of antimicrobial agents, are important and ongoing needs. The present invention will be seen to meet these and other needs.

SUMMARY OF THE INVENTION

The present invention relates to carrier systems useful for pharmaceutical compositions. The present invention relates to a pharmaceutical carrier comprising an emulsifier, and in further embodiments also comprising a polymeric dissolution aid. The present invention also relates to a pharmaceutical composition further comprising a pharmaceutical active. The present invention also relates to a pharmaceutical composition wherein said pharmaceutical active is an antimicrobial agent. The present invention also relates to methods for making pharmaceutical carriers and compositions.

The present invention provides a method of treating a microbial infection in a patient comprising administering a pharmaceutically effective amount of a pharmaceutical composition of the present invention. The present invention provides a method of preventing a microbial infection in a patient comprising administering a prophylactically effective amount of a pharmaceutical composition of the present invention. The present invention provides a method of reducing the risk of a microbial infection in a patient comprising administering a prophylactically effective amount of a pharmaceutical composition of the present invention.

The present invention provides compositions useful for treating, preventing, or reducing the risk of a microbial infection in a patient.

The present invention provides the use of an antimicrobial agent in the manufacture of a pharmaceutical composition or medicament useful for treating, preventing, or reducing the risk of a microbial infection in a patient.

The present invention provides a method, composition, or use wherein the composition, compared to a control composition, provides at least a 5% improvement in dissolution in a two step dissolution testing system.

The present invention provides a method, composition, or use wherein the composition, compared to a control composition, provides at least a 5% improvement in dissolution in a two step dissolution testing testing, wherein the two step dissolution system comprises measuring the dissolution in a first step in a simulated gastric environment of about pH 4 for up to 30 minutes followed by measuring the dissolution in a second step in a simulated gastric environment of about pH 5.4 to about 6.5 for up to about 60 minutes.

The foregoing and other aspects and embodiments of the present invention can be more fully understood by reference to the following detailed description and claims.

DETAILED DESCRIPTION OF THE INVENTION

Figure 1:
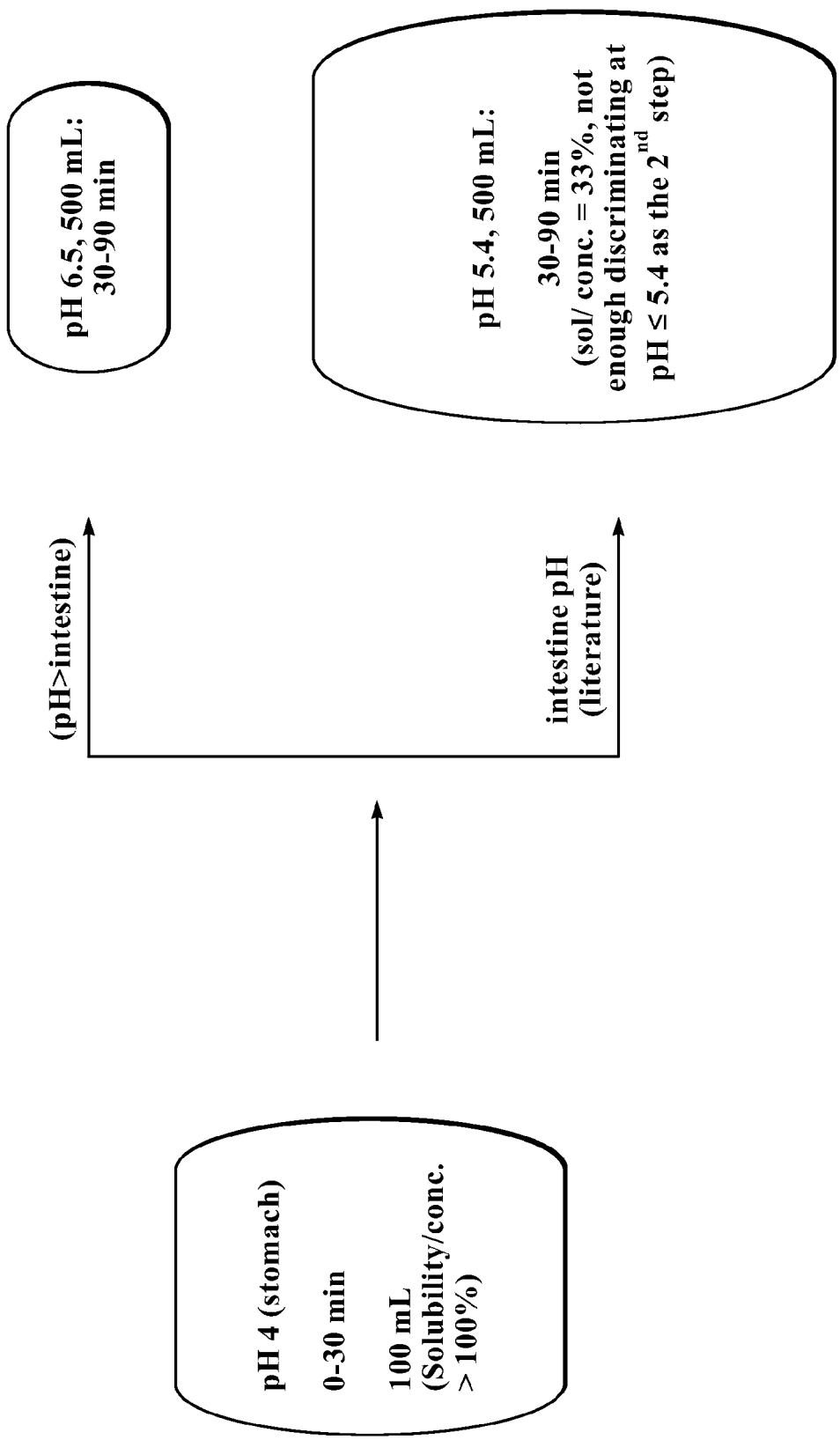
FIG. 1 depicts a schematic of the two-step dissolution testing of a drug in a simulated gastrointestinal system as described in Section C of the Example Dissolution Testing in a Simulated Gastrointestinal System.

The present invention relates to carrier systems useful for pharmaceutical compositions. The present invention relates to a carrier system for a pharmaceutical composition comprising an emulsifier, and in further embodiments also comprising a polymeric dissolution aid.

1. DEFINITIONS

The terms "carrier" or "carrier system" means one or more compatible substances that are suitable for delivering, containing, or "carrying" a pharmaceutical active ingredient for administration to a patient or subject.

The terms "patient" or "subject", as used herein, means a human or animal (in the case of an animal, more typically a mammal such as domesticated mammal, or animals such as poultry animals and fish and other seafood or freshwater food creatures) that would be considered to be in need of the pharmaceutical compositions of the present invention or of the methods of treating, preventing, or reducing the risk of a microbial infection.

As used herein, the term "effective amount" refers to an amount of a pharmaceutical active compound, or a combination of compounds, for example an antimicrobial agent or agents, when administered alone or in combination, to treat, prevent, or reduce the risk of a disease state or condition, for example a microbial infection. The term also refers to an amount of a pharmaceutical composition containing an active compound or combination of compounds. For example, an effective amount refers to an amount of the compound present in a formulation given to a recipient patient or subject sufficient to elicit biological activity, for example, anti-infective activity, such as e.g., anti-microbial activity or anti-bacterial activity.

As used herein, the phrase "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

As used herein, the term "pharmaceutically effective amount" refers to an amount of a pharmaceutical active compound, or a combination of compounds, for example an antimicrobial agent or agents, when administered alone or in combination, to treat, prevent, or reduce the risk of a disease state or condition, for example a microbial infection. The term also refers to an amount of a pharmaceutical composition containing an active compound or combination of compounds. For example, a pharmaceutically effective amount refers to an amount of the pharmaceutical active present in a pharmaceutical composition or formulation of the present invention or on a medical device containing a composition or formulation of the present invention given to a recipient patient or subject sufficient to elicit biological activity, for example, activity against a microbial infection.

The term "prophylactically effective amount" means an effective amount of a pharmaceutical active compound, or a combination of compounds, for example an antimicrobial agent or agents, when administered alone or in combination, to prevent, or reduce the risk of a disease state or condition, for example a microbial infection—in other words, an amount to give a preventative or prophylactic effect. The term also refers to an amount of a pharmaceutical composition containing an active compound or combination of compounds.

The term "treating", as used herein, means to cure an already present disease state or condition, e.g. a microbial infection in a patient or subject. Treating can also include inhibiting, i.e. arresting the development of a disease state or condition, e.g. a microbial infection, and relieving or ameliorating, i.e. causing regression of the disease state or condition, e.g. a microbial infection.

The term "preventing", as used herein means, to completely or almost completely stop a disease state or condition, e.g. a microbial infection, from occurring in a patient or subject, especially when the patient or subject is predisposed to such or at risk of contracting a disease state or condition, e.g., a microbial infection. Preventing can also include inhibiting, i.e. arresting the development, of a disease state or condition, e.g., a microbial infection, and relieving or ameliorating, i.e. causing regression of the disease state or condition, e.g., a microbial infection, for example when the disease state or condition, e.g., a microbial infection, may already be present.

The term "reducing the risk of", as used herein, means to lower the likelihood or probability of a disease state or condition, e.g., a microbial infection, from occurring in a patient or subject, especially when the patient or subject is predisposed to such or at risk of contracting a disease state or condition, e.g., a microbial infection.

One or ordinary skill in the art will appreciate that there is some overlap in the definitions of "treating", "preventing", and "reducing the risk of".

As used herein, the teen "tablet" is intended to encompass compressed pharmaceutical dosages formulations of all shapes and sizes whether coated or uncoated.

As used herein, the term "capsule" is intended to encompass pharmaceutical dosages forms enclosed in a shell, e.g. a gelatin shell such as a soft gelatin or hard gelatin capsule.

The chemical compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present invention and intermediates made therein are, where appropriate, considered to be part of the present invention. All tautomers of shown or described compounds are also, where appropriate, considered to be part of the present invention.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

As used herein, "pharmaceutically acceptable salts" refer to derivatives of the pharmaceutical active compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed. (Mack Publishing Company, 1990) and Remington: *The Science and Practice of Pharmacy*, 20th Edition, Baltimore, Md.: Lippincott Williams & Wilkins, 2000, which are incorporated by reference herein in their entirety. For example, salts can include, but are not limited to, the hydrochloride and acetate salts of the aliphatic amine-containing, hydroxylamine-containing, and imine-containing compounds of the present invention.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation, and as appropriate, purification from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

2. COMPOSITIONS OF THE PRESENT INVENTION

The carriers of the compositions of the present invention comprise the following essential and optional components. The compositions of the present invention also comprise a pharmaceutical active, which is described further below.

Suitable carrier components are described in e.g., Eds. R. C. Rowe, et al., Handbook of Pharmaceutical Excipients, Fifth Edition, Pharmaceutical Press (2006); *Remington's Pharmaceutical Sciences*, 18th ed. (Mack Publishing Company, 1990); and Remington: *The Science and Practice of Pharmacy*, 20th Edition, Baltimore, Md.: Lippincott Williams & Wilkins, 2000, which are incorporated by reference herein in their entirety. Even though a functional category can be provided for many of these carrier components, such a functional category is not intended to limit the function or scope of the component, as one of ordinary skill in the art will recognize that a component can belong to more than one functional category and that the level of a specific component and the presence of other components can effect the functional properties of a component.

a. Emulsifier

The compositions of the present invention in further embodiments further comprise an emulsifier. Useful emulsifier include polyglycolized glycerides (also known as polyglycolysed glycerides). These materials are generally surface active and depending on their exact composition have a range of melting points and hydrophilic/lipophilic balance ranges (HLBs). These materials are often further combined with a polyhydric alcohol, such as glycerol. The polyglycolized glycerides are mixtures of glycerides of fatty acids and of esters of polyoxyethylene with fatty acids. In these mixtures, the fatty acids are generally saturated or unsaturated $C_8$-$C_{22}$, for example $C_8$-$C_{12}$ or $C_{16}$-$C_{20}$. The glycerides are generally monoglycerides, diglycerides, or triglycerides or mixtures thereof in any proportions. Polyglycolysed glycerides are marketed e.g., by Gattefosse under the trade names Labrafil, Labrosol, and Gelucire. The Gelucire polyglycolized glycerides are often designated with the melting point and HLB. For example, Gelucire 53/10 refers to a material having a melting point of 53° C. and an HLB of 10. Gelucire materials useful herein include Gelucire 44/14 and Gelucire 50/13. Other emulsfiers useful herein include vitamin E TPGS, ploxamers, and lecithin. Vitamin E TPGS is also known as d-α-tocopheryl polyethylene glycol 1000 succinate.

Ploxamers are known by the trade name Pluronics, and are nonionic triblock copolymers composed of a central hydrophobic chain of polyoxypropylene (poly(propylene oxide)) flanked by two hydrophilic chains of polyoxyethylene (poly(ethylene oxide)).

The emulsifier can comprise from about 0.1% to about 99.9% of the compositions of the present invention. In other embodiments, the emulsifier can comprise from about 1% to about 20%, from about 1% to about 15%, and from about 1% to about 10% of the compositions of the present invention.

b. Polymeric Dissolution Aid

The compositions of the present invention comprise a polymeric dissolution aid. Such polymeric dissolution aids include polymers of 1-ethenyl-2-pyrrolidinone; polyamine N-oxide polymers; copolymers of N-vinylpyrrolidone and N-vinylimidazole; polyvinyloxazolidones and polyvinylimidazoles or mixtures thereof. Particularly useful are polymers of 1-ethenyl-2-pyrrolidinone, especially the homopolymer. Generally this homopolymer has a molecular weight range of about 2500 to 3,000,000. This homopolymer is known as polyvinylpyrrolidone, PVP, or povidone and in other instances can function as a dissolution aid, disintegrant, suspending agent, or binder.

The polymeric dissolution aid can comprise from about 0.1% to about 99.9% of the compositions of the present invention. In other embodiments, the polymeric dissolution aid can comprise from about 1% to about 10%, from about 1% to about 5%, and from about 1% to about 2.5% of the compositions of the present invention.

c. Binder

The compositions of the present invention can further comprise a binder or binding agent. Examples of binders are cellulose; microcrystalline cellulose; low viscosity water soluble cellulose derivatives such as microcrystalline cellulose, hydroxypropyl cellulose, hydroxypropylmethyl cellulose (HPMC), hydroxyethyl cellulose, ethyl cellulose, methyl cellulose, and sodium carboxy-methyl cellulose; alginic acid derivatives; polyvinylpyrrolidone; magnesium aluminum silicate; starches such as corn starch and potato starch; gelatin; and tragacanth. A preferred binder is HPMC. Preferably the binding agent comprises from about 1 to about 10%. Preferably, the binder comprises from about 1 to about 4% by weight of the composition.

d. pH Modifier

The compositions of the present invention can further comprise a pH modifier. Examples of pH modifiers are generally acidic or basic materials that can be used to modify or adjust the pH of the formulation or its environment. Nonlimiting examples of pH modifiers useful herein include aspartic acid, citric acid, ethanesulfonic acid, fumaric acid, lactic acid, methanesulfonic acid, tartaric acid, and mixtures thereof.

e. Filler

The compositions of the present invention can further comprise a filler. Examples of fillers are microcrystalline cellulose; glucose; lactose; dextrose; mannitol; sorbitol; sucrose; starches; fumed silica; salts such as sodium carbonate and calcium carbonate; and polyols such as propylene glycol. Preferably, fillers are present in an amount of from 0% to about 50% by weight of the composition, either alone or in combination. More preferably they are present from about 5% to about 20% of the weight of the composition.

f. Dispersing or Wetting Agent

The compositions of the present invention can further comprise a dispersing or wetting agent. Examples of dispersing or wetting agents are polymers such as polyethylene-polypropylene, and surfactants such as sodium lauryl sulfate. Preferably the dispersing or wetting agent is present in an amount of from 0% to about 50% by weight, either alone or in combination. More preferably they are present from about 5% to about 20% of the weight of the composition.

g. Disintegrant

The compositions of the present invention can further comprise a disintegrant. Examples of disintegrants are modified starches or modified cellulose polymers, e.g. sodium starch glycolate. Other disintegrants include agar; alginic acid and the sodium salt thereof; effervescent mixtures (e.g., the combination of an acid such as tartaric acid or citric acid and a basic salt such as sodium or potassium bicarbonate, which upon contact with an aqueous environment react to produce carbon dioxide bubbles which help to break up or disintegrate the composition); croscarmelose; crospovidone; sodium carboxymethyl starch; sodium starch glycolate; clays; and ion exchange resins. Preferably the disintegrant is present in an amount of from 0% to about 50% by weight of the composition, either alone or in combination. More preferably the disintegrant is present from about 5% to about 20% by weight of the composition.

h. Lubricant

The compositions of the present invention can further comprise a lubricant. Generally, the lubricant is selected from a long chain fatty acid or a salt of a long chain fatty acid. Suitable lubricants are exemplified by solid lubricants including silica; talc; stearic acid and its magnesium salts and calcium salts; calcium sulfate; and liquid lubricants such as polyethylene glycol; and vegetable oils such as peanut oil, cottonseed oil, sesame oil, olive oil, corn oil and oil of *theobroma*. Preferably the lubricant is present in an amount of from 0% to about 50% by weight of the composition, either alone or in combination. More preferably it is present from about 5% to about 20% of the weight of the composition.

i. Additional Components

The compositions of the present invention can further comprise one or more additional components selected from a wide variety of excipients known in the pharmaceutical formulation art. According to the desired properties of the tablet or capsule, any number of ingredients can be selected, alone or in combination, based upon their known uses in preparing the compositions of the present invention. Such ingredients include, but are not limited to, water; nonaqueous solvents (e.g. ethanol); coatings; capsule shells; colorants; waxes, gelatin; flavorings; preservatives (e.g., methyl paraben, sodium benzoate, and potassium benzoate); antioxidants [e.g., butylated hydroxyanisole ("BHA"), butylated hydroxytoluene ("BHT"), and vitamin E and vitamin E esters such as tocopherol acetate]; flavor enhancers; sweeteners (e.g., aspartame and saccharin); compression aids; surfactants, etc.

3. PHARMACEUTICAL ACTIVES AND ANTIMICROBIAL AGENTS OF THE PRESENT INVENTION

The pharmaceutical compositions of the present invention comprise a pharmaceutical carrier and one or more pharmaceutical actives. A wide range of pharmaceutical actives can be used depending on the desired therapeutic class and disease or condition to be treated, prevented, or of which one desires to reduce the risk of. Pharmaceutically acceptable salts, esters, and prodrug thereof of these pharmaceutical actives are contemplated as within the scope of the invention.

In one embodiment of the present invention, the pharmaceutical active is an antimicrobial agent or compound. A wide range of antimicrobial agents can be used in the methods, compositions, and uses of the present invention. These antimicrobial agents can provide their therapeutic effect by a variety of biochemical or biophysical mechanisms. Such agents useful in the present invention can include those which bind to or modulate ribosomal RNA, for example bacterial ribosomal RNA. Such agents also useful in the present invention can include those which bind to or modulate the large ribosomal subunit, for example the large ribosomal subunit of a bacterial organism. Such agents also useful in the present invention can include those which bind to or modulate DNA topoisomerases, for example bacterial DNA topoisomerases. Such agents also useful in the present invention can include those which bind to or modulate bacterial DNA gyrase, for example bacterial DNA gyrase, i.e. gyrase being an example of a topoisomerase. Such agents also useful in the present invention can include those which bind to or modulate bacterial topoisomerase IV.

Useful antimicrobial agents include antibacterial agents, antifungal agents, anti-viral agents, and anti-parasitic agents. Useful chemical classes of compounds include those selected from oxazolidinones (e.g., linezolid, eperezolid, N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide, and other oxazolidinones), macrolides, ketolides, streptogramin As, streptogramin Bs, chloramphenicol and chloramphenicol derivatives, fluorfenicol and fluorfenicol derivatives, glycopeptides, pleuromutilins, aminoglycosides, beta-lactams and carbapenems (including carbapenems with a 7-acylated imidazo[5-1,b]thiazole-2-yl group directly attached to the carbapenem moiety of the C-2 position), cephalosporins, lincosamides, quinolones and fluoroquinolones (e.g., pyridinecarboxylic acid derivatives, garenoxacin, gatifloxacin, gemifloxacin, levofloxacin, moxifloxacin, etc.), benzoheterocyclic compounds, aminomethylcycline compounds, dalbavancin, daptomycin, oritavancin, televancin, and mixtures thereof. It should be noted that compounds useful herein can in some instances be classified in more than one way. The description or classification of a compound or compounds is not intended to limit that compound or compounds, but is being done for the sake of convenience.

The compounds useful in the present invention can include the pharmaceutically acceptable salts, esters, or prodrugs thereof. The invention further provides methods for synthesizing any one of the compounds of the present invention. The invention also provides pharmaceutical compositions comprising an effective amount of one or more of the compounds of the present invention and a pharmaceutically acceptable carrier. The present invention further provides methods for making these compounds, carriers, and pharmaceutical compositions.

Oxazolidinones

Oxazolidinones and their pharmaceutically acceptable salts, esters, and prodrugs thereof, can be used in the methods, compositions, and uses of the present invention. Linezolid, i.e. (N-[[(5S)-3-[3-fluoro-4-(4-morpholinyl) phenyl]-2-oxo-5-oxazolidinyl]methyl]acetamide), which is sold under the trade name or proprietary name Zyvox, is a commercially marketed oxazolidinone. See U.S. Pat. No. 6,559,305 B1, to Bergren, issued May 6, 2003; U.S. Pat. No. 5,688,792, to Barbachyn et al., issued Nov. 18, 1997; and M. R. Barbychan et al., "Development of Linezolid: Oxazolidinone Structure-Activity Relationships Leading to Linezolid", Angew. Chem. Int. Ed., 42, pp. 2010-2023 (2003). Other oxazolidinones and other compounds useful in the methods, compositions, and uses of the present invention are described in U.S. Pat. No. 6,969,726 B2, to Lou et al., issued Nov. 29, 2005; PCT Application No. WO 2006/022794, to Rib-X Pharmaceuticals, Inc., published Mar. 2, 2006; PCT Application No. WO 2005/070904, to Rib-X Pharmaceuticals, Inc., published Aug. 4, 2005; PCT Application No. WO 2005/061468, to Rib-X Pharmaceuticals, Inc., published Jul. 7, 2005; PCT Application No. WO 2005/019211, to Rib-X Pharmaceuticals, Inc., published Mar. 3, 2005; PCT Application No. WO 2005/012271, to Rib-X Pharmaceuticals, Inc., published Feb. 10, 2005; PCT Application No. WO 2005/012270, to Rib-X Pharmaceuticals, Inc., published Feb. 10, 2005; U.S. Patent Application Publication No. US 2005/0043317 A1, to Zhou et al., published Feb. 24, 2005; U.S. Patent Application Publication No. US 2005/0153971 A1, to Chen et al., published Jul. 14, 2005; U.S. Pat. No. 5,654,435 to Barbachyn et al., issued Aug. 5, 1997 and, PCT Application No. WO 2001/094342, to Dong A Pharm. Co., Ltd., published Dec. 13, 2001, and PCT Application No., WO 01/081350, to AstraZeneca AB and AstraZeneca UK Limited, published Nov. 1, 2001.

Nonlimiting examples of oxazolidiones include those selected from the group consisting of the following compounds A 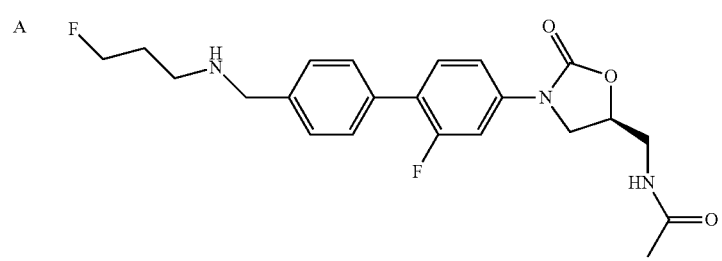

(5S)-N-(3-{2-Fluoro-4'-[(3-fluoro-propylamino)-methyl]-biphenyl-4-yl}-2-oxo-oxazolidin-5-ylmethyl)-acetamide B 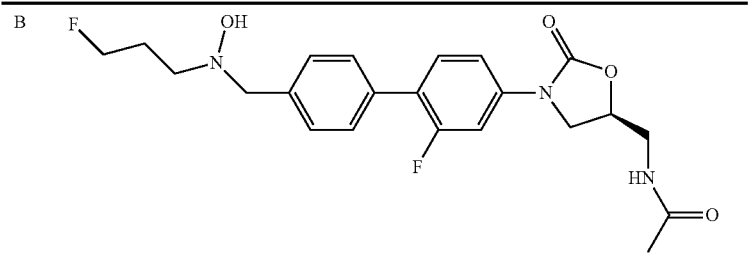

(5S)-N-[3-(2-Fluoro-4'-{[(3-fluoro-propyl)-hydroxy-amino]-methyl}-biphenyl-4-yl)-2-oxo-oxazolidin-5-ylmethyl]-acetamide C 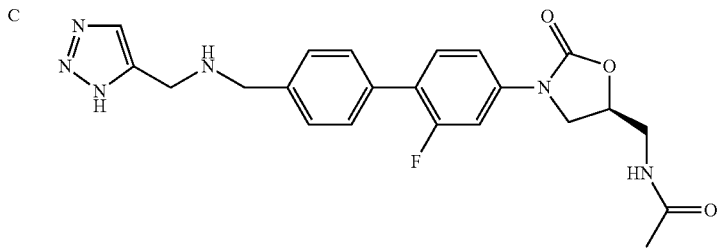

N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-acetamide D 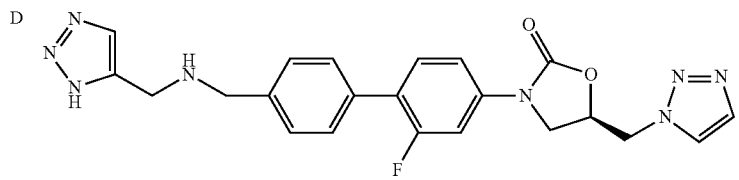

3-(2-Fluoro-4'-{[(3H-[1,2,3]triazol-4-ylmethyl)-amino]-methyl}-biphenyl-4-yl)-5-(R)-[1,2,3]triazol-1-ylmethyl-oxazolidin-2-one E 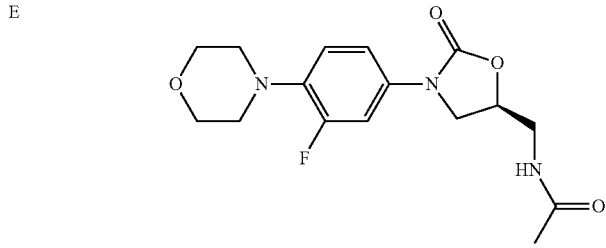

Linezolid or (S)-N-[[3-[3-Fluoro-4-(4-morpholinyl)phenyl]-2-oxo-5-oxazolidinyl] methyl]-acetamide or a pharmaceutically acceptable salt, ester, or prodrug thereof. An example of a salt would be the monohydrochloride salt of the foregoing oxazolidinones A, B, C, and D.

For compound C, above, the following numbering convention can be used in which the triazole ring is attached at the "4" position to the remainder of the compound, and where the remaining carbon atom at position "5" of the triazole ring is unsubstituted, i.e. where it has a hydrogen, is as follows:

Compound C

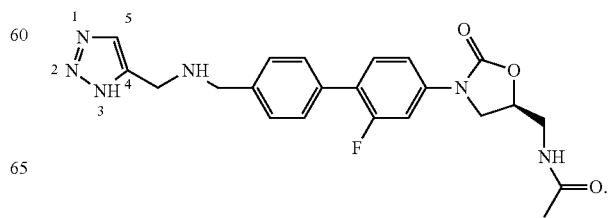

It should be recognized that the triazole ring is a 5-membered heteroaromatic ring and that the location of the two double bonds drawn in most representations is an arbitrary depiction of one of the multiple structures that can be drawn, and is used for convenience and not intended as a limitation. In fact, five different structures, sometimes called tautomeric structures, can be drawn to depict a 1,2,3-triazole. These tautomeric structures can be indicated with double-headed arrows between each structure, indicating that the molecules so represented are in equilibrium with each other. For example, for Compound C, the following tautomeric structures can be drawn:

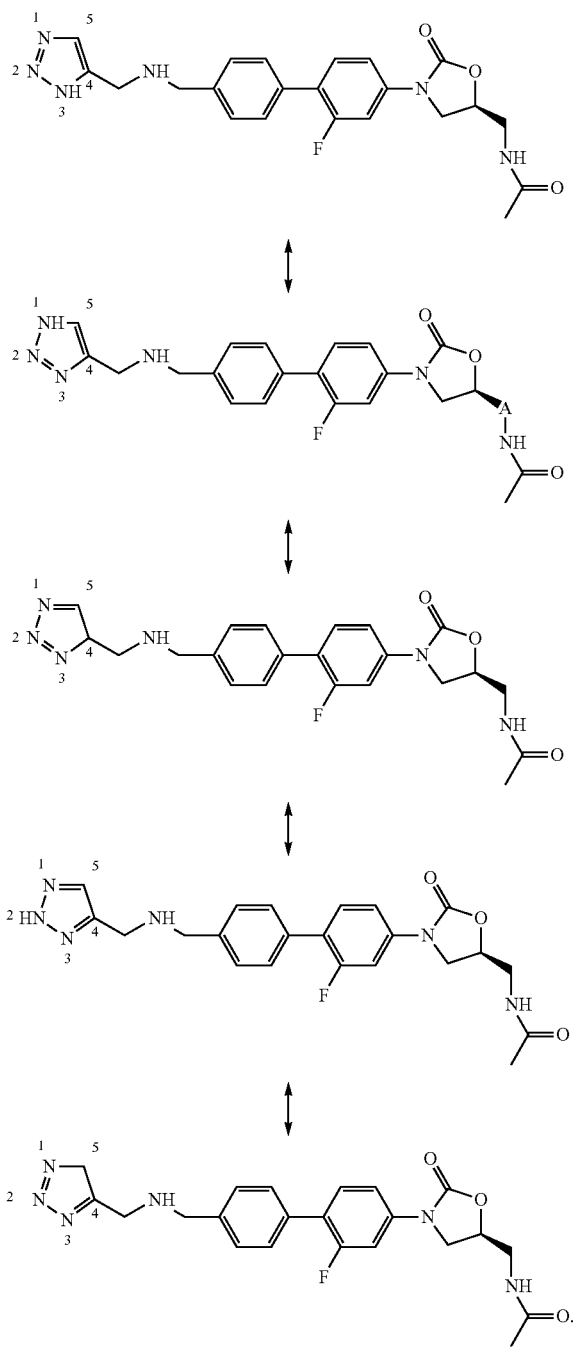

Tautomeric Structures for Compound C

Further disclosure on oxazolidinones useful herein and compounds such as oxazolidinones C and D are found in U.S. Pat. No. 6,969,726 B2, to Lou et al., issued Nov. 29, 2005, cited above. Compound C, is also known by the chemical name: Acetamide, N-[[(5S)-3-(2-Fluoro-4'-[[(1H-1,2,3-triazole-4-ylmethyl)-amino]methyl][1,1'-biphenyl]-4-yl]-2-oxo-5-oxazolidinyl]-methyl]-, and has the CAS registry number 869884-78-6. The monohydrochloride salt of compound C is also known by the chemical name: Acetamide, N-[[(5S)-3-(2-Fluoro-4'-[[(1H-1,2,3-triazole-4-ylmethyl)-amino]methyl][1,1'-biphenyl]-4-yl]-2-oxo-5-oxazolidinyl]-methyl]-, monohydrochloride, and has the CAS registry number 869884-77-5.

These and other oxazolidinones relate to a compound having the formula:

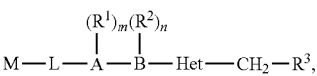

or a pharmaceutically acceptable salt, ester or prodrug thereof, wherein:

A is selected from the group consisting of:
phenyl, pyridyl, pyrazinyl, pyrimidinyl, and pyridazinyl;
B is selected from the group consisting of:
phenyl, pyridyl, pyrazinyl, pyrimidinyl, and pyridazinyl;
Het-$CH_2$—$R^3$ is selected from the group consisting of:

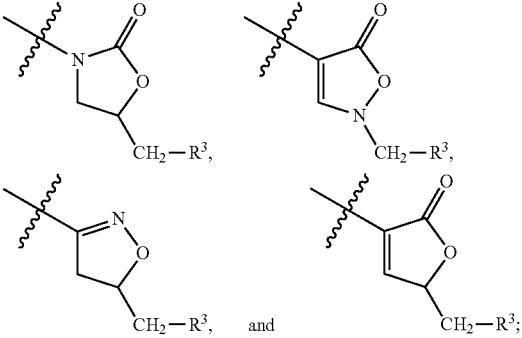

M is selected from the group consisting of:
a) saturated, unsaturated, or aromatic $C_{3-14}$ carbocycle, and
b) saturated, unsaturated, or aromatic 3-14 membered heterocycle containing one or more heteroatoms selected from the group consisting of nitrogen, oxygen, and sulfur,
wherein a) or b) optionally is substituted with one or more $R^5$ groups;

M-L is selected from the group consisting of:
a) M-X, b) M-$L^1$, c) M-$L^1$-X, d) M-X-$L^2$, e) M-$L^1$-X-$L^2$, f) M-X-$L^1$-X-$L^2$, g) M-$L^1$-X-$L^2$-X, h) M-X-X-, i) M-$L^1$-X-X-, j) M-X-X-$L^2$, and k) M-$L^1$-X-X-$L^2$, wherein X, at each occurrence, independently is selected from the group consisting of:
a) —O—, b) —$NR^4$—, c) —N(O)—, d) —N(O$R^4$)—, e) —S(O)$_p$—, f) —SO$_2$$NR^4$—, g) —$NR^4$SO$_2$—, h) —$NR^4$—N═, i) ═N—$NR^4$—, j) —O—N═, k) ═N—O—, l) —N═, m) ═N—, n) —$NR^4$—$NR^4$—, o) —$NR^4$C(O)O—, p) —OC(O)$NR^4$—, q) —$NR^4$C(O)$NR^4$— r) —$NR^4$C($NR^4$)$NR^4$—, and s)

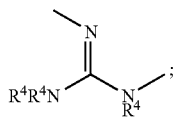

$L^1$ is selected from the group consisting of:
   a) $C_{1-6}$ alkyl, b) $C_{2-6}$ alkenyl, and c) $C_{2-6}$ alkynyl,
      wherein any of a)-c) optionally is substituted with one or more $R^5$ groups; and $L^2$ is selected from the group consisting of:
   a) $C_{1-6}$ alkyl, b) $C_{2-6}$ alkenyl, and c) $C_{7-6}$ alkynyl,
      wherein any of a)-c) optionally is substituted with one or more $R^5$ groups;

$R^1$, at each occurrence, independently is selected from the group consisting of:
   a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)_pR^4$, bb) —$SO_2NR^4R^4$, and cc) $R^4$;

$R^2$, at each occurrence, independently is selected from the group consisting of:
   a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)_pR^4$, bb) —$SO_2NR^4R^4$, and cc) $R^4$;

$R^3$ is selected from the group consisting of:
   a) —$OR^4$, b) —$NR^4R^4$, c) —$C(O)R^4$, d) —$C(O)OR^4$, e) —$OC(O)R^4$, f) —$C(O)NR^4R^4$, g) —$NR^4C(O)R^4$, h) —$OC(O)NR^4R^4$, i) —$NR^4C(O)OR^4$, j) —$NR^4C(O)NR^4R^4$, k) —$C(S)R^4$, l) —$C(S)OR^4$, m) —$OC(S)R^4$, n) —$C(S)NR^4R^4$, o) —$NR^4C(S)R^4$, p) —$OC(S)NR^4R^4$, q) —$NR^4C(S)OR^4$, r) —$NR^4C(S)NR^4R^4$, s) —$NR^4C(NR^4)NR^4R^4$, t) —$S(O)_pR^4$, u) —$SO_2NR^4R^4$, and v) $R^4$;

$R^4$, at each occurrence, independently is selected from the group consisting of:
   a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(±)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
   wherein any of b)-p) optionally is substituted with one or more $R^5$ groups;

$R^5$, at each occurrence, is independently selected from the group consisting of:
   a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —$C(O)R^6$, p) —$C(O)OR^6$, q) —$OC(O)R^6$, r) —$C(O)NR^6R^6$, s) —$NR^6C(O)R^6$, t) —$OC(O)NR^6R^6$, u) —$NR^6C(O)OR^6$, v) —$NR^6C(O)NR^6R^6$, w) —$C(S)R^6$, x) —$C(S)OR^6$, y) —$OC(S)R^6$, z) —$C(S)NR^6R^6$, aa) —$NR^6C(S)R^6$, bb) —$OC(S)NR^6R^6$, cc) —$NR^6C(S)OR^6$, dd) —$NR^6C(S)NR^6R^6$, ee) —$NR^6C(NR^6)NR^6R^6$, ff) —$S(O)_pR^6$, gg) —$SO_2NR^6R^6$, and hh) $R^6$;

$R^6$, at each occurrence, independently is selected from the group consisting of:
   a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(±)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
   wherein any of b)-p) optionally is substituted with one or more $R^7$ groups;

$R^7$, at each occurrence, independently is selected from the group consisting of:
   a) F, b) Cl, c) Br, d) I, e) =O, f) g) =$NR^8$, h) =$NOR^8$, i) =N—$NR^8R^8$, j) —$CF_3$, k) —$OR^8$, l) —CN, m) —$NO_2$, n) —$NR^8R^8$, o) —$C(O)R^8$, p) —$C(O)OR^8$, q) —$OC(O)R^8$, r) —$C(O)NR^8R^8$, s) —$NR^8C(O)R^8$, t) —$OC(O)NR^8R^8$, u) —$NR^8C(O)OR^8$, v) —$NR^8C(O)NR^8R^8$, w) —$C(S)R^8$, x) —$C(S)OR^8$, y) —$OC(S)R^8$, z) —$C(S)NR^8R^8$, aa) —$NR^8C(S)R^8$, bb) —$OC(S)NR^8R^8$, cc) —$NR^8C(S)OR^8$, dd) —$NR^8C(S)NR^8R^8$, ee) —$NR^8C(NR^8)NR^8R^8$, ff) —$S(O)_pR^8$, gg) —$SO_2NR^8R^8$, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and 11) 3-14 membered saturated, unsaturated, or aromatic, heterocycle comprising one or more heteroatoms selected from the group consisting of nitrogen, oxygen, and sulfur,
   wherein any of hh)-ii) optionally is substituted with one or more moieties selected from the group consisting of $R^8$, F, Cl, Br, I, —$CF_3$, —$OR^8$, —$SR^8$, —CN, —$NO_2$, —$NR^8R^8$, —$C(O)R^8$, —$C(O)OR^8$, —$OC(O)R^8$, —$C(O)NR^8R^8$, —$NR^8C(O)R^8$, —$OC(O)NR^8R^8$, —$NR^8C(O)OR^8$, —$NR^8C(O)NR^8R^8$, —$C(S)R^8$, —$C(S)OR^8$, —$OC(S)R^8$, —$C(S)NR^8R^8$, —$NR^8C(S)R^8$, —$OC(S)NR^8R^8$, —$NR^8C(S)OR^8$, —$NR^8C(S)NR^8R^8$, —$NR^8C(NR^8)NR^8R^8$, —$SO_2NR^8R^8$, and —$S(O)_pR^8$;

$R^8$, at each occurrence, independently is selected from the group consisting of:

a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —$CF_3$, —OH, —$OCH_3$, —SH, —$SCH_3$, —CN, —$NO_2$, —$NHCH_3$, —$N(CH_3)_2$, —$C(O)CH_3$, $C(O)OCH_3$, —$C(O)NH_2$, —$NHC(O)CH_3$, —$SO_2NH_2$, —$SO_2NHCH_3$, —$SO_2N(CH_3)_2$, and —$S(O)_pCH_3$;

m, at each occurrence, independently is 0, 1, 2, 3, or 4;
n, at each occurrence, independently is 0, 1, 2, 3, or 4; and
p, at each occurrence, independently is 0, 1, or 2.

Particular embodiments of the invention include compounds having the formula:

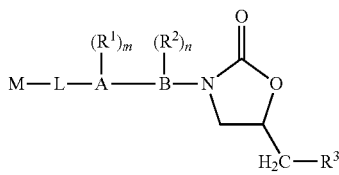

or a pharmaceutically acceptable salt, ester or prodrug thereof, wherein A, B, L, M, $R^1$, $R^2$, $R^3$, m, and n are defined above.

Other embodiments include compounds having the formula:

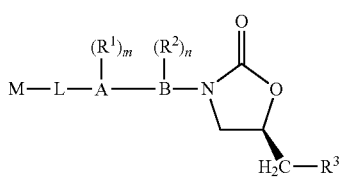

or a pharmaceutically acceptable salt, ester or prodrug thereof, wherein A, B, L, M, $R^1$, $R^2$, $R^3$, m, and n are defined as described above.

Particular compounds include those where A is selected from the group consisting of phenyl and pyridyl; B is selected from the group consisting of phenyl and pyridyl; m is 0, 1, or 2; and n is 0, 1, or 2.

In some embodiments, A-B is:

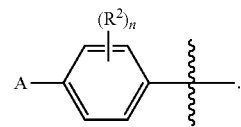

wherein A, $R^2$, and n are defined as described above. In particular embodiments, A-B is:

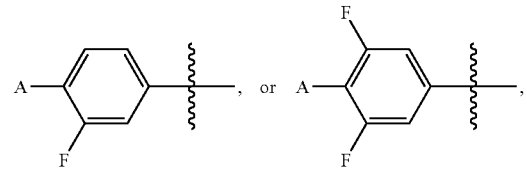

wherein A is defined as described above.

In various embodiments, A-B is:

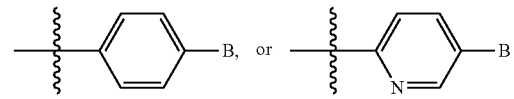

wherein B is defined as described in above.

In some embodiments, $R^3$ is —NHC(O)$R^4$. Particular compounds according to these embodiments include those where $R^4$ is —$CH_3$. In other embodiments, $R^3$ is:

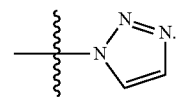

Particular embodiments of the invention include compounds having the formula:

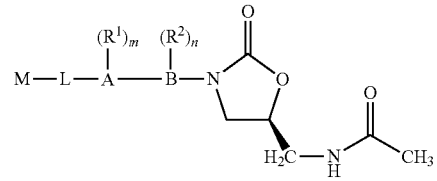

or a pharmaceutically acceptable salt, ester or prodrug thereof, wherein A, B, L, M, $R^1$, $R^2$, m, and n are defined as described above.

Other embodiments of the invention include compounds having the formula:

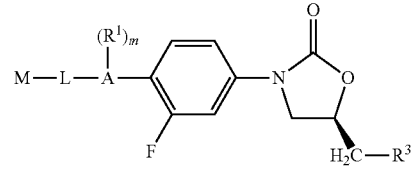

or a pharmaceutically acceptable salt, ester or prodrug thereof, wherein A, L, M, $R^1$, $R^3$, and m are defined as described above.

Still other embodiments of the invention include compounds having the formula:

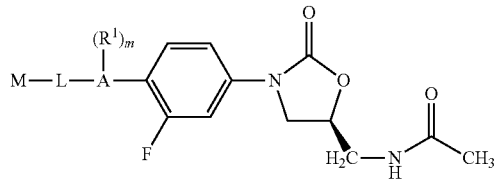

or a pharmaceutically acceptable salt, ester or prodrug thereof, wherein A, L, M, $R^1$, and m are defined as described above.

Some embodiments of the invention include compounds having the formula:

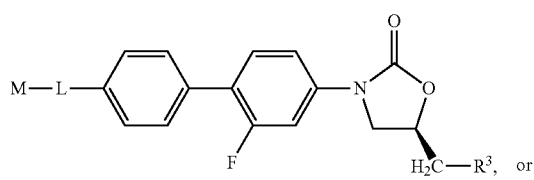

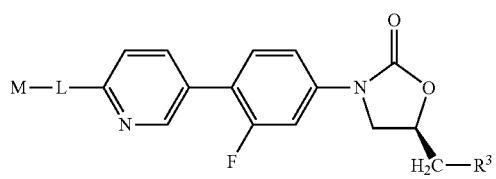

or a pharmaceutically acceptable salt, ester or prodrug thereof, wherein L, M, and $R^3$ are defined as described above. Particular compounds according to these embodiments include those wherein $R^3$ is —NHC(O)CH$_3$.

Other embodiments of the invention include compounds having the formula:

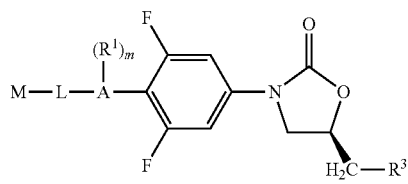

or a pharmaceutically acceptable salt, ester or prodrug thereof, wherein A, L, M, $R^1$, $R^3$, and m are defined as described above.

Still other embodiments of the invention include compounds having the formula:

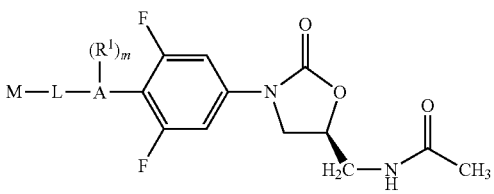

or a pharmaceutically acceptable salt, ester or prodrug thereof, wherein A, L, M, $R^1$, and m are defined as described above.

Some embodiments of the invention include compounds having the formula:

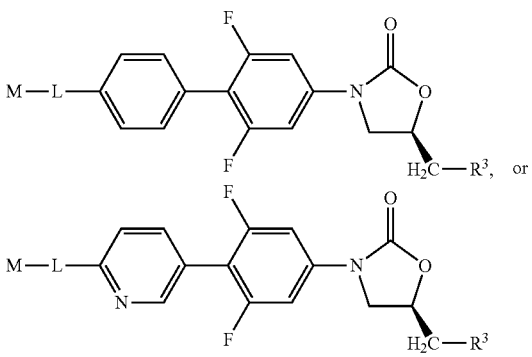

or a pharmaceutically acceptable salt, ester or prodrug thereof, wherein L, M, and $R^3$ are defined as described above. Particular compounds according to these embodiments include those wherein $R^3$ is —NHC(O)CH$_3$.

In some embodiments, M-L is M-$L^1$, and $L^1$ is $C_{1-6}$ alkyl. In particular embodiments, M-$L^1$ is M-CH$_2$—.

In other embodiments, M-L is M-$L^1$-X-$L^2$, and X is —NR$^4$—. In particular compounds according to these embodiments, X is —NH—, —N(O)—, or —N(OR$^4$)—, where $R^4$ is H or $C_{1-6}$ alkyl. Other compounds include those where X is

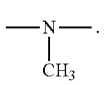

In certain compounds according to these embodiments, $L^1$ is $C_{1-6}$ alkyl, and $L^2$ is $C_{1-6}$ alkyl. In some embodiments, $L^1$ is —CH$_2$— and $L^2$ is —CH$_2$—. Particular examples of compounds according to these embodiments include those where M-L is M-CH$_2$—NH—CH$_2$— or

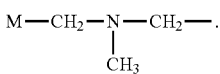

In still other embodiments, M-L is M-S-$L^1$-NR$^4$— $L^2$, wherein $L^1$ is $C_{1-6}$ alkyl, and $L^2$ is $C_{1-6}$ alkyl. In particular compounds according to these embodiments, M-L is M-S—CH$_2$CH$_2$—NH—CH$_2$—.

In particular embodiments, M is selected from the group consisting of:

a) phenyl, b) pyridyl, c) pyrazinyl, d) pyrimidinyl, e) pyridazinyl, f) oxiranyl, g) aziridinyl, h) furanyl, i) thiophenyl, j) pyrrolyl, k) oxazolyl, l) isoxazolyl, m) imidazolyl, n) pyrazolyl, o) isothiazolyl, p) thiazolyl, q) triazolyl, r) tetrazolyl, s) indolyl, t) purinyl, u) benzofuranyl, v) benzoxazolyl, w) benzisoxazolyl, x) quinolinyl, y) isoquinolinyl, z) quinoxalinyl, aa) quinazolinyl. bb) cinnolinyl, cc) cyclopropyl, dd) cyclobutyl, ee) cyclopentyl, ff) cyclohexyl, gg) cycloheptyl, hh) oxetanyl, ii) tetrahydrofuranyl, jj) tetrahydropyranyl, kk) azetidinyl, ll) pyrrolidinyl, m) piperidinyl, m) thietanyl, oo) tetrahydrothiophenyl, pp) tetrahydrothiopyranyl, qq) piperazinyl, m) quinuclidinyl, ss) 1-azabicyclo[2.2.1]hyeptanyl, tt) morpholinyl, uu) thiomorpholinyl, vv) thiooxomorpholinyl, ww) thiodioxomorpholinyl, and xx) benzothiophenyl wherein any of a)-xx) optionally is substituted with one or more $R^5$ groups. In particular embodiments, M is 4-isoxazolyl, [1,2,3]triazol-1-yl, 3H-[1,2,3]triazol-4-yl, 1H-tetrazol-5-yl, piperidin-1-yl, or pyrrolidin-1-yl.

In preferred embodiments, A is phenyl, substituted phenyl, pyridyl, or substituted pyridyl. Under certain circumstances, when A is pyridin-4-yl substituted with M-L at the 2 position, M-L is not (imidazol-1-yl)methyl or (morpholin-4-yl)methyl.

In preferred embodiments, B is phenyl or substituted phenyl. More preferably, B is substituted phenyl. Preferred substituents include halogens, and in particular, fluorine. Under certain circumstances, when B is unsubstituted phenyl, M-L is selected from the group consisting of M-X, M-$L^1$-X, M-$L^1$-X-$L^2$, M-X-$L^1$-X-$L^2$, M-X-X-, M-$L^1$-X-X-, M-X-X-$L^2$, and M-$L^1$-X-X-$L^2$. Under certain circumstances, when B is pyridin-2-yl substituted with A at the 5 position, M-L is selected from the group consisting of M-X, M-$L^1$-X-$L^2$-X, M-X-X-, M-X-X-$L^2$, and M-$L^1$-X-X-$L^2$.

Quinolones and Fluoroquinolones

Quinolone derivatives, such as pyridonecarboyxlic acid derivatives, useful herein are described, including their synthesis, formulation, and use, in U.S. Pat. No. 6,156,903, to Yazaki et al., issued Dec. 5, 2000 and its certificate of correction of Dec. 11, 2001; U.S. Pat. No. 6,133,284, to Yazaki et al., issued Oct. 17, 2000; U.S. Pat. No. 5,998,436, to Yazaki et al., issued Dec. 7, 1999 and its certificate of corrections of Jan. 23, 2001 and Dec. 17, 2002; PCT Application No. WO 2006/042034, to Abbott Laboratories, published Apr. 20, 2006, PCT Application No. WO 2006/015194, to Abbott Laboratories, published Feb. 9, 2006; PCT Application No. WO 01/34595, to Wakunaga Pharmaceutical Co., Ltd., published May 17, 2001; and PCT Application No. WO 97/11068, to Wakunaga Pharmaceutical Co., Ltd., published Mar. 27, 1997.

Pyridonecarboxylic acid derivatives of the methods, compositions, and uses of the present invention include compounds corresponding to the following structure (Pyridonecarboxylic Acid Derivative 1)

Pyridonecarboxylic Acid Derivative 1

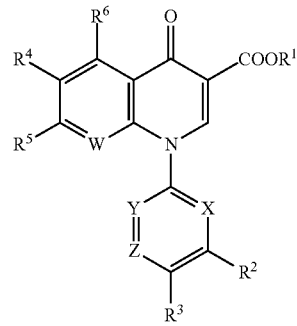

wherein $R^1$ represents a hydrogen atom or a carboxyl protective group; $R^2$ represents a hydroxyl group, a lower alkoxy group, or a substituted or unsubstituted amino group; $R^3$ represents a hydrogen atom or a halogen atom; $R^4$ represents a hydrogen atom or a halogen atom; $R^5$ represents a halogen atom or an optionally substituted saturated cyclic amino group; $R^6$ represents a hydrogen atom, a halogen atom, a nitro group, or an optionally protected amino group; X, Y and Z may be the same or different and respectively represent a nitrogen atom, CH or $CR^7$ (wherein $R^7$ represents a lower alkyl group, a halogen atom, or a cyano group), with the proviso that at least one of X, Y and Z represent a nitrogen atom, and W represents a nitrogen atom or $CR^8$ (wherein $R^8$ represents a hydrogen atom, a halogen atom, or a lower alkyl group), and with the proviso that when $R^1$ represents a hydrogen atom, $R^2$ represents an amino group, $R^3$ and $R^4$ represent a fluorine atom, $R^6$ represents a hydrogen atom, X represents a nitrogen atom, Y represents $CR^7$ (wherein $R^7$ represents a fluorine atom), Z represents CH, and W is $CR^8$ (wherein $R^8$ represents a chlorine atom), then $R^5$ is not a 3-hydroxyazetidine-1-yl group;

or a pharmaceutically acceptable salt, ester, or prodrug thereof.

As described in the foregoing paragraph, when $R^1$ is a carboxyl protective group, it may be any carboxylate ester residue which cleaves relatively easily to generate the corresponding free carboxyl group. Exemplary carboxyl protective groups include those which may be eliminated by hydrolysis, catalytic reduction, and other treatments under mild conditions such as lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups such as benzyl group; and aryl groups such as phenyl group and naphthyl group; and those which may be readily eliminated in the body such as lower alkanoyloxy lower alkyl groups such as acetoxymethyl group and pivaloyloxymethyl group; lower alkoxycarbonyloxy lower alkyl group such as methoxycarbonyloxymethyl group and 1-ethoxycarbonyloxyethyl group; lower alkoxymethyl group such as methoxymethyl group; lactonyl group such as phthalidyl; di-lower alkylamino lower alkyl group such as 1-dimethylaminoethyl group; and (5-methyl-2-oxo-1,3-dioxole-4-yl)methyl group.

It is noted that the substituents $R^1$, $R^2$, $R^3$, $R^4$, $R^5$, $R^6$, $R^7$, $R^8$, $R^9$, A, $J^1$, $J^2$, $J^3$, W, Z, e, f, and g are defined herein for convenience with respect to the chemical structure for the pyridonecarboxylic acid derivatives, e.g., Pyridonecarboxylic Acid Derivative 1, and do not refer to other substituents for other compounds of the present invention.

In other embodiments, the present invention relates to a method, composition, or use for a pyridonecarboxylic acid derivative of structure Pyridonecarboxylic Acid Derivative 1, wherein W is $CR^8$, wherein $R^8$ represents a hydrogen atom, a halogen atom, or a lower alkyl group.

In other embodiments, the present invention relates to a method, composition, or use for a pyridonecarboxylic acid derivative of structure Pyridonecarboxylic Acid Derivative 1, wherein $R^5$ is a group represented by the following formula (a) or (b):

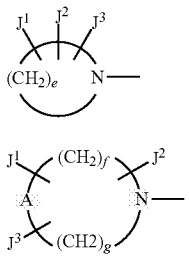

wherein A represents an oxygen atom, sulfur atom or $NR^9$ (wherein $R^9$ represents hydrogen atom or a lower alkyl group), e represents a number from 3 to 5, f represents a number from 1 to 3, g represents a number from 0 to 2, $J^1$, $J^2$ and $J^3$, which may be the same or different from one another, represent a hydrogen atom, hydroxyl group, lower alkyl group, amino lower alkyl group, amino group, lower alkylamino group, lower alkoxy group, or a halogen atom.

In other embodiments, the present invention relates to a method, composition, or use for a pyridonecarboxylic acid derivative of structure Pyridonecarboxylic Acid Derivative 1, wherein $R^5$ is a group represented by formula (a).

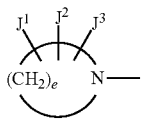

In other embodiments, the present invention relates to a method, composition, or use for a pyridonecarboxylic acid derivative of structure Pyridonecarboxylic Acid Derivative 1, wherein e in the formula (a) is 3 or 4.

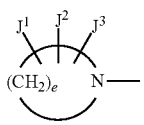

In other embodiments, the present invention relates to a method, composition, or use for a pyridonecarboxylic acid derivative of structure Pyridonecarboxylic Acid Derivative 1, wherein $R^1$ is a hydrogen atom; $R^2$ is an amino group, lower alkylamino group, or a di-lower alkylamino group; $R^3$ is a halogen atom; $R^4$ is a halogen atom; $R^6$ is hydrogen atom; X is a nitrogen atom; Y and Z are CH or $CR^7$ (wherein $R^7$ is a lower alkyl group or a halogen atom); and W is $CR^8$ (wherein $R^8$ is a halogen atom or a lower alkyl group).

In other embodiments, the present invention relates to a method, composition, or use for a pyridonecarboxylic acid derivative of structure Pyridonecarboxylic Acid Derivative 1, wherein $R^2$ is amino group; $R^3$ is fluorine atom; $R^4$ is a fluorine atom; Y is CF; Z is CH; W is $CR^8$ (wherein $R^8$ is a chlorine atom, bromine atom or a methyl group), and e in formula (a) is 3.

In other embodiments, the present invention relates to a method, composition, or use wherein said pyridonecarboxylic acid corresponds to the following structure:

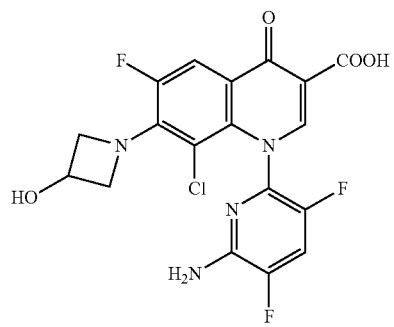 [SMILES: Nc1nc(-n2cc(C(=O)O)c(=O)c3cc(F)c(N4CC(O)C4)c(Cl)c32)c(F)cc1F]

or a pharmaceutically acceptable salt, ester, or prodrug thereof. This foregoing pyridonecarboxylic acid is also known by the publicly disclosed code names ABT-492 and WQ 3034 and also by the chemical name 1-(6-amino-3,5-difluoro-2-pyridinyl)-8-chloro-6-fluoro-1,4-dihydro-7-(3-hydroxy-1-azetidinyl)-4-oxo-3-quinolinecarboxylic acid or 1-(6-amino-3,5-difluoro-2-pyridinyl)-8-chloro-6-fluoro-1,4-dihydro-7-(3-hydroxyazetidine-1-yl)-4-oxo-3-quinolinecarboxylic acid. This carboxylic acid form of the compound corresponds to the CAS registry number 189279-58-1. Furthermore, WO 2006/042034, cited above discloses the D-glucitol salt of this compound [D-glucitol 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt)] and the trihydrate of the D-glucitol salt of this compound [D-glucitol 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt)]. The D-glucitol salt and the D-glucitol salt trihydrate correspond to the CAS registry numbers 352458-37-8 and 883105-02-0, respectively. D-glucitol corresponds to the CAS registry number 6284-40-8. WO 2006/042034 also discloses a crystalline form of the D-glucitol salt characterized when measured at about 25° C. with Cu-Ka radiation, by the powder diffraction pattern shown in FIG. 1 of WO 2006/042034 and a crystalline form of the D-glucitol salt trihydrate when measured at about 25° C. with Cu-Ka radiation, by the powder diffraction pattern shown in FIG. 2 of WO 2006/042034. These D-glucitol salts are useful in the present invention. Also, see A. R. Haight et al., "Synthesis of the Quinolone ABT-492: Crystallizations for Optimal Processing", Organic Process Research & Development (2006), 10(4), 751-756.

Other quinolone compounds useful herein, include fluoroquinolones such as garenoxacin, gatifloxacin, gemilfoxacin, levofloxacin, and moxifloxacin.

Garenoxacin and its pharmaceutically acceptable salts, esters, and prodrugs thereof, can be used in the methods, compositions, and uses of the present invention. Garenoxacin is also known as 1-cyclopropyl-8-(difluoromethoxy)-7-(1R)-(1-methyl-2,3-dihydro-1H-5-isoinodyl)-4-oxo-1,4-dihydro-3-quinolinecarboxylic acid methanesulfonate monohydrate and by the publicly disclosed code names T-3811 and BM 284756. See M. Takahata et al., "In Vitro and In Vivo Antimicrobial Activities of T-3811 ME, a Novel Des-F(6)-Quinolone", Antimicrobial Agents and Chemotherapy, vol. 43, no. 5, pp. 1077-1084 (1999); U.S. Pat. No. 6,025,370, to Todo et al, issued Feb. 15, 2000; and U.S. Pat. No. 5,935,952, to Todo et al., issued Aug. 10, 1999 and its certificate of correction of Dec. 5, 2000.

Gatifloxacin and its pharmaceutically acceptable salts, esters, and prodrugs thereof, can be used in the methods, compositions, and uses of the present invention. Gatifloxacin is sold under the trade name or proprietary Tequin. See U.S. Pat. No. 6,589,955 B2, to Raghavan et al., issued Jul. 8, 2003; U.S. Pat. No. 5,880,283, to Matsumoto et al., issued Mar. 9, 1999; and U.S. Pat. No. 4,980,470, to Masuzawa et al., issued Dec. 25, 1990 and its certificate of correction of Aug. 11, 1992.

Gemifloxacin and its pharmaceutically acceptable salts, esters, and prodrugs thereof, can be used in the methods, compositions, and uses of the present invention. Gemifloxacin is sold under the trade name or proprietary Factive. See U.S. Pat. No. 6,803,376 B1, to Appelbaum et al., issued Oct. 12, 2004; U.S. Pat. No. 6,723,734 B2, to Kim et al., issued Apr. 20, 2004; U.S. Pat. No. 6,455,540 B1, to Citron et al., issued Sep. 24, 2002; U.S. Pat. No. 6,340,689 B1, to Dubois et al., issued Jan. 22, 2002 and its certificate of correction of Jun. 18, 2002; U.S. Pat. No. 6,331,550 B1, to Citron et al., issued Dec. 18, 2001; U.S. Pat. No. 6,262,071 B1, to Crabb et al., issued Jul. 17, 2001; U.S. Pat. No. 5,962,468, to Hong et al., issued Oct. 5, 1999 and its certificate of correction of May 9, 2000; U.S. Pat. No. 5,776,944, to Hong et al., issued Jul. 7, 1998; and U.S. Pat. No. 5,633,262, to Hong et al., issued May 27, 1997.

Levofloxacin and its pharmaceutically acceptable salts, esters, and prodrugs thereof, can be used in the methods, compositions, and uses of the present invention. Levofloxacin is sold under the trade name or proprietary Levaquin. See U.S. Pat. No. 5,053,407, to Hayakawa et al., issued Oct. 1, 1991 and its certificate of correction of Sep. 27, 1994.

Moxifloxacin and its pharmaceutically acceptable salts, esters, and prodrugs thereof, can be used in the methods, compositions, and uses of the present invention. Moxifloxacin is sold under the trade name or proprietary Avelox. See U.S. Pat. No. 5,849,752, to Grunenberg et al., issued Dec. 15, 1998; U.S. Pat. No. 5,607,942, to Petersen et al., issued Mar. 4, 1997; and U.S. Pat. No. 4,990,517, to Petersen et al., issued Feb. 5, 1991 and its certificate of correction of Apr. 25, 1995.

Benzoheterocyclic Compounds

Benzoheterocyclic compounds useful herein are described, including their synthesis, formulation, and use, in U.S. Pat. No. 6,753,333 B2, to De Souza et al., issued Jun. 22, 2004; U.S. Pat. No. 6,750,224 B1, to Patel et al, issued Jun. 15, 2004 and its certificate of correction of Nov. 2, 2004; U.S. Pat. No. 6,664,267 B1, to de Souza et al., issued Dec. 16, 2003; U.S. Pat. No. 6,608,078 B2, to De Souza et al., issued Aug. 19, 2003; U.S. Pat. No. 6,514,986 B2 to De Souza et al., issued Feb. 4, 2003; U.S. Pat. No. 4,552,879 to Ishikawa et al., issued Nov. 12, 1985; and U.S. Pat. No. 4,399,134 to Ishikawa et al., issued Aug. 16, 1983.

Benzoheterocyclic compounds of the methods, compositions, and uses of the present invention include compounds corresponding to the following structure (Benzoheterocyclic Compound I)

Benzoheterocyclic Compound I

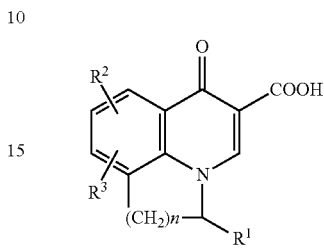

wherein $R^1$ represents a hydrogen atom or a lower alkyl group; $R^2$ represents a hydrogen atom or a halogen atom; $R^3$ represents a 1-pyrrolidinyl group which may be substituted with a hydroxymethyl group, a 1,2,5,6-tetrahydro-1-pyridyl group, or a group of the formula

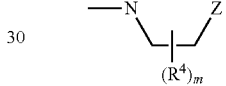

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is an integer of 1 or 2; or a pharmaceutically acceptable salt ester or prodrug thereof.

It is noted that the substituents $R^1$, $R^2$, $R^3$, $R^4$, Z, m, and n are defined herein for convenience with respect to the chemical structure for the benzoheterocyclic compounds, e.g., benzoheterocyclic compound (I) and do not refer to other substituents for other compounds of the present invention.

In other embodiments, the present invention relates to a method, composition, or use for a benzoheterocyclic of structure Benzoheterocyclic Compound I, wherein n is 2.

In other embodiments, the present invention relates to a method, composition, or use for a benzoheterocyclic of structure Benzoheterocyclic Compound I, wherein n is 1.

In other embodiments, the present invention relates to a method, composition, or use for a benzoheterocyclic of structure Benzoheterocyclic Compound I, wherein $R^3$ represents a group of the formula

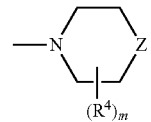

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is 1.

In other embodiments, the present invention relates to a method, composition, or use for a benzoheterocyclic of structure Benzoheterocyclic Compound I, wherein $R^3$ represents a 1-pyrrolidinyl group which may be substituted with a hydroxymethyl group or a 1,2,5,6-tetrahydro-1-pyridyl group.

In other embodiments, the present invention relates to a method, composition, or use for a benzoheterocyclic of structure Benzoheterocyclic Compound I, wherein $R^4$ represents a hydrogen atom, a hydroxy group or a lower alkanoyloxy group and the position at which the group of the formula

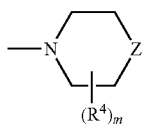

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is 1, is attached is the 8-position.

In other embodiments, the present invention relates to a method, composition, or use for a benzoheterocyclic of structure Benzoheterocyclic Compound I, wherein $R^4$ represents a lower alkyl group, a lower alkoxy group, a phenyl-lower alkyl group, an amino group which may be substituted with a lower alkyl group or a lower alkanoyl group, an oxo group, a carbamoyl group, and the position at which the group of the formula

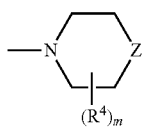

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is 1, is attached is the 8-position.

In other embodiments, the present invention relates to a method, composition, or use for a benzoheterocyclic of structure Benzoheterocyclic Compound I, wherein $R^2$ represents a halogen atom.

In other embodiments, the present invention relates to a method, composition, or use for a benzoheterocyclic of structure Benzoheterocyclic Compound I, wherein $R^2$ represents a hydrogen atom.

In other embodiments, the present invention relates to a method, composition, or use for a benzoheterocyclic of structure Benzoheterocyclic Compound I, wherein $R^2$ represents a fluorine atom and the position at which the fluorine atom is attached is the 9-position.

In other embodiments, the present invention relates to a method, composition, or use for a benzoheterocyclic of structure Benzoheterocyclic Compound I, wherein $R^2$ represents a chlorine atom and the position at which the fluorine atom is attached is the 9-position.

In other embodiments, the present invention relates to a method, composition, or use for a benzoheterocyclic of structure Benzoheterocyclic Compound I, wherein $R^1$ represents a lower alkyl group.

In other embodiments, the present invention relates to a method, composition, or use for a benzoheterocyclic of structure Benzoheterocyclic Compound I, wherein $R^1$ represents a methyl group.

In other embodiments, the present invention relates to a method, composition, or use for a benzoheterocyclic of structure Benzoheterocyclic Compound I, wherein $R^2$ represents a fluorine atom attached to the 9-position and $R^1$ represents a methyl group.

In other embodiments, the present invention relates to a method, composition, or use for a benzoheterocyclic of structure Benzoheterocyclic Compound I, wherein $R^1$ represents a methyl group, $R^2$ represents a fluorine atom attached to the 9-position and the position at which the group represented by $R^3$ is attached is the 8-position.

In other embodiments, the present invention relates to a method, composition, or use for a benzoheterocyclic of structure Benzoheterocyclic Compound I, wherein the position at which $R^3$ is attached is the 9-position.

In other embodiments, the present invention relates to a method, composition, or use for a benzoheterocyclic of structure Benzoheterocyclic Compound I, wherein $R^1$ represents a methyl group, $R^2$ represents a fluorine atom attached to the 8-position.

In other embodiments, the present invention relates to a method, composition, or use for a benzoheterocyclic of structure Benzoheterocyclic Compound I, wherein $R^1$ represents a methyl group, $R^2$ represents a chlorine atom attached to the 8-position.

In other embodiments, the present invention relates to a method, composition, or use wherein said benzoheterocyclic compound is 9-fluoro-8-(4-hydroxy-1-piperidyl)-5-methyl-6,7-dihydro-1-oxo-1H,5H-benzo[i,j]quinolizine-2-carboxylic acid or a pharmaceutically acceptable salt, ester, or prodrug thereof.

In other embodiments, the present invention relates to a method, composition, or use wherein said benzoheterocyclic compound is S(±)-9-fluoro-6,7-dihydro-8-(4-hydroxypiperidin-1-yl)-5-methyl-1-oxo-1H,5H-benzo[i,j]quinolizine-2-carboxylic acid or a pharmaceutically acceptable salt, ester, or prodrug thereof. The foregoing compound is also known by the chemical name nadifloxacin.

In other embodiments, the present invention relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt.

In other embodiments, the present invention relates to a method, composition, or use wherein said benzoheterocyclic compound is a specific polymorph or crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt.

In other embodiments, the present invention relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 10.16, 11.78, 12, 52, 16.00, 18.94, 19.66, 20.36, 21.28, 21.92, 22.52, 24.74, 25.28, 30.74.

In other embodiments, the present invention relates to a method, composition, or use wherein said benzoheterocyclic compound is (−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 18.28, 18.8, 19.8, 20.12, 20.62, 21.10, 21.44, 21.88, 22.6, 23.02.

In other embodiments, the present invention relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 14.02±0.2, 14.82±0.2, 19.28±0.2, 22.12±0.2, 22.96±0.2, 23.46±0.2, 28.36±0.2.

With respect to specific polymorph or crystalline forms of the benzoheterocyclic compounds, examples being the arginine salts, a publicly disclosed code name for such a compound is WCK 771.

Beta-Lactams

Beta-lactams, for example carbapenems, examples of which are carbapenems with a 7-acylated imidazo[5-1,b]thiazole-2-yl group directly attached to the carbapenem moiety of the C-2 position, useful herein are described, including their synthesis, formulation, and use, in M. Kurazano et al., "In Vitro Activities of ME1036 (CP5609), a Novel Parenteral Carbapenem, Against Methicillin-Resistant Staphylococci", Antimicrobial Agents and Chemotherapy, vol. 48, no. 8, pp. 2831-2837 (August 2004); U.S. Patent Application Publication No. US 2004/0038967 A1, to Kano et al., published Feb. 26, 2004; PCT Application No. WO 2004/055027, to Meiji Seika Kaisha, Ltd., published Jul. 1, 2004; and PCT Application No. WO 02/042312, to Meiji Seika Kaisha, Ltd., published May 30, 2002.

Beta-lactam compounds of the methods, compositions, and uses of the present invention include compounds corresponding to the following structure (Beta-Lactam I)

Beta-Lactam I

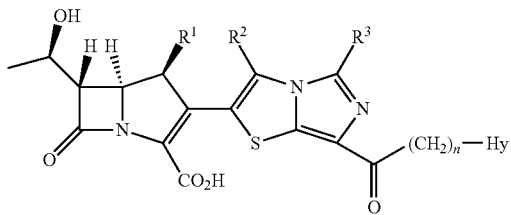

wherein $R^1$ represents a hydrogen atom or methyl, $R^2$ and $R^3$, which may be the same or different, each represent a hydrogen atom; a halogen atom; lower alkyl optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; lower cycloalkyl; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; carbamoyl; aryl optionally substituted by amino optionally substituted by one or two lower alkyl groups; lower alkylthio wherein the alkyl portion of lower alkylthio is optionally substituted by amino, hydroxyl, azide, a halogen atom, cyano, carbamoyl, formylamino, lower alkylcarbonylamino, aminosulfonylamino, or lower alkylthio; morpholinyl; lower alkylsulfonyl; or formyl; n is an integer of 0 to 4, and Hy represents a four- to seven-membered monocyclic or nine- or ten-membered bicyclic saturated or unsaturated heterocyclic group having one to four heteroatoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom; hydroxyl; carbamoyl; carboxylmethyl-substituted carbamoyl; amino; N,N-di-lower alkylamino; aryl optionally substituted by amino; a monocyclic or bicyclic heterocyclic group containing one or more hetero-atoms selected from nitrogen, oxygen, and sulfur atoms, optionally substituted by aminosulfonyl or carboxyl; carboxyl; imino; lower alkoxycarbonyl; lower alkylcarbonyl; aminosulfonylamino; amino lower alkylthio; lower alkylsulfonyl; (N,N-di-lower alkylamino)sulfonylamino; N'—(N,N-di-lower alkylamino)sulfonyl-N'-lower alkylamino; halogenated lower alkylcarbonyl; N-aminosulfonylpiperidinyl; and cyano; lower alkylthio wherein one or more hydrogen atoms on the alkyl group are optionally substituted by a group selected from a halogen atom, hydroxyl, carbamoyl, amino, and aryl; lower alkylsulfonyl wherein one or more hydrogen atoms on the alkyl group are optionally substituted by a group selected from a halogen atom, hydroxyl, carbamoyl, amino, 1-iminoethylamino, and aryl; hydroxyl; lower alkoxy; hydroxyaminophenyl-substituted lower alkoxy; halogenated lower alkoxy; aminophenyl-substituted lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino-; (N,N-di-lower alkylamino)sulfonylamino; aryl; or a monocyclic or bicyclic heterocyclic group containing one or more hetero-atoms selected from nitrogen, oxygen, and sulfur atoms, optionally substituted by aminosulfonyl or carboxyl, or a pharmaceutically acceptable salt, ester or pro-drug thereof.

It is noted that the substituents $R^2$, $R^3$, Hy, and n are defined herein for convenience with respect to the chemical structure for the beta-lactams or carbapenems, e.g., Beta-Lactam I and Beta-Lactam II, and do not refer to other substituents for other compounds of the present invention.

In other embodiments, the present invention relates to a method, composition, or use for a beta-lactam of structure Beta-Lactam I, wherein $R^1$ represents a hydrogen atom or methyl, $R^2$ and $R^3$, which may be the same or different, each represent a hydrogen atom; a halogen atom; lower alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; aryl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio, n is an integer of 0 to 4, and Hy represents a four- to seven-membered monocyclic or nine- or ten-membered bicyclic saturated or unsaturated heterocyclic group containing one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkyl aminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl; or a monocyclic or bicyclic heterocyclic group containing one or more hetero-atoms selected from nitrogen, oxygen, and sulfur atoms.

In other embodiments, the present invention relates to a method, composition, or use of a beta-lactam of structure Beta-Lactam I wherein $R^1$ represents a hydrogen atom or methyl, $R^2$ and $R^3$, which may be the same or different, each represent a hydrogen atom, a halogen atom, optionally substituted lower alkyl, lower cycloalkyl, lower alkylcarbonyl, carbamoyl, optionally substituted aryl, optionally substituted lower alkylthio, morpholinyl, lower alkylsulfonyl, or formyl, n is an integer of 0 to 2, and Hy represents a group selected from optionally substituted pyridinyl, optionally substituted pyridinium-yl, optionally substituted tetrahydropyridinyl, optionally substituted thiazolyl, optionally substituted pyrimidinyl, optionally substituted thienyl, optionally substituted quinolinyl, optionally substituted quinolinium-yl, optionally substituted isoquinolinyl, optionally substituted dihydroisoquinolinyl, optionally substituted piperazinyl, optionally substituted piperidinyl, optionally substituted indolyl, optionally substituted thiomorpholinyl, optionally substituted imidazolyl, and optionally substituted pyrrolidinyl.

In other embodiments, the present invention relates to a method, composition, or use of a beta-lactam of structure Beta-Lactam I wherein $R^1$ represents a hydrogen atom or methyl, $R^2$ and $R^3$, which may be the same or different, each represent a hydrogen atom, a halogen atom, optionally substituted lower alkyl, optionally substituted lower alkylcarbonyl, carbamoyl, aryl, or optionally substituted lower alkylthio, n is an integer of 0 to 4, and Hy represents a group selected from optionally substituted pyridinyl, optionally substituted pyridinium-yl, optionally substituted tetrahydropyridinyl, optionally substituted thiazolyl, optionally substituted pyrimidinyl, optionally substituted thienyl, optionally substituted quinolinyl, optionally substituted quinolinium-yl, and optionally substituted pyrrolidinyl.

In other embodiments, the present invention relates to Beta-lactam compounds of the methods, compositions, and uses of the present invention include compounds corresponding to the following structure (Beta-Lactam II)

Beta-Lactam II

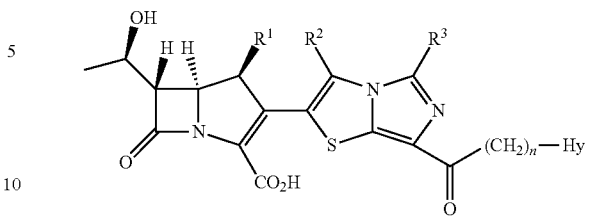

wherein $R^1$ represents a hydrogen atom or methyl, $R^2$ and $R^3$, which may be the same or different, each represent a hydrogen atom; a halogen atom; lower alkyl optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; lower cycloalkyl; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; carbamoyl; aryl optionally substituted by amino optionally substituted by one or two lower alkyl groups; lower alkylthio wherein the alkyl portion of lower alkylthio is optionally substituted by amino, hydroxyl, azide, a halogen atom, cyano, carbamoyl, formylamino, lower alkylcarbonylamino, aminosulfonylamino, or lower alkylthio; morpholinyl; lower alkylsulfonyl; or formyl; n is an integer of 0 to 4, and Hy represents a four- to seven-membered monocyclic or nine- or ten-membered bicyclic saturated or unsaturated heterocyclic group having one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom; hydroxyl; carbamoyl; carboxylmethyl-substituted carbamoyl; amino; N,N-di-lower alkylamino; aryl optionally substituted by amino; a monocyclic or bicyclic heterocyclic group containing one or more hetero-atoms selected from nitrogen, oxygen, and sulfur atoms, optionally substituted by aminosulfonyl or carboxyl; carboxyl; imino; lower alkoxycarbonyl; lower alkylcarbonyl; aminosulfonylamino; amino lower alkylthio; lower alkylsulfonyl; (N,N-di-lower alkylamino)sulfonylamino; N'—(N,N-di-lower alkylamino)sulfonyl-N'-lower alkylamino; halogenated lower alkylcarbonyl; N-aminosulfonylpiperidinyl; and cyano; lower alkylthio wherein one or more hydrogen atoms on the alkyl group are optionally substituted by a group selected from a halogen atom, hydroxyl, carbamoyl, amino, and aryl; lower alkylsulfonyl wherein one or more hydrogen atoms on the alkyl group are optionally substituted by a group selected from a halogen atom, hydroxyl, carbamoyl, amino, 1-iminoethylamino, and aryl; hydroxyl; lower alkoxy; hydroxyaminophenyl-substituted lower alkoxy; halogenated lower alkoxy; aminophenyl-substituted lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino-; (N,N-di-lower alkylamino)sulfonylamino; aryl; or a monocyclic or bicyclic heterocyclic group containing one or more hetero-atoms selected from nitrogen, oxygen, and sulfur atoms, optionally substituted by aminosulfonyl or carboxyl, or a pharmaceutically acceptable salt, ester, or prodrug thereof.

In other embodiments, the present invention relates to a method, composition, or use of a beta-lactam of structure Beta-Lactam II, wherein $R^1$ represents a hydrogen atom or methyl, $R^2$ and $R^3$, which may be the same or different, each represent a hydrogen atom, a halogen atom, lower alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; aryl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio, n is an integer of 0 to 4, and Hy represents a four- to seven-membered monocyclic or nine- or ten-membered bicyclic saturated or unsaturated heterocyclic group containing one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl; or a monocyclic or bicyclic heterocyclic group containing one or more hetero-atoms selected from nitrogen, oxygen, and sulfur atoms.

In other embodiments, the present invention relates to a method, composition, or use of a beta-lactam of structure Beta-Lactam I or Beta-Lactam II, wherein the substituent on the lower alkyl and lower alkylcarbonyl groups optionally represented by $R^2$ and $R^3$ is hydroxyl, lower alkoxy, N,N-di-lower alkylamino, or N-carbamoyl lower alkyl-N,N-di-lower alkylammonino, the substituent on the aryl group optionally represented by $R^2$ and $R^3$ is N,N-di-lower alkylamino, the substituent on the lower alkylthio group optionally represented by $R^2$ and $R^3$ is amino, hydroxyl, or azide, and the substituent on the saturated or unsaturated heterocyclic ring represented by Hy is lower alkyl optionally substituted by carboxyl methyl-substituted carbamoyl, carbamoyl, phenyl, aminophenyl, N,N-di-lower alkylamino, amino, hydroxyl, morpholinyl, pyrrolidinyl, carboxyl, imino, amino lower alkylthio, lower alkoxycarbonyl, lower alkylcarbonyl, aminosulfonylamino, piperidinyl, lower alkylsulfonyl, (N,N-di-lower alkylamino)sulfonylamino, N'—(N,N-di-lower alkylamino)sulfonyl-N'-lower alkylamino, halogenated lower alkylcarbonyl, N-aminosulfonylpiperidinyl, or cyano; carbamoyl; pyridinyl; N-aminosulfonylpyrrolidinyl; 2-carboxypyrrolidinyl; phenyl; hydroxyl; lower alkoxy; hydroxyaminophenyl-substituted lower alkoxy; halogenated lower alkoxy; aminophenyl-substituted lower alkoxy; amino; carboxyl; lower alkylthio optionally substituted by amino; amino lower alkylthio; amino lower alkylsulfonyl; or 1-iminoethylamino lower alkylsulfonyl.

In other embodiments, the present invention relates to a method, composition, or use of a beta-lactam of structure Beta-Lactam I or Beta-Lactam II, wherein $R^1$ represents a hydrogen atom or methyl, $R^2$ and $R^3$ represent a hydrogen atom, n is 0 (zero), and Hy represents pyridinium-yl having carbamoylmethyl at its 1-position.

In other embodiments, the present invention relates to a method, composition, or use of a beta-lactam of structure Beta-Lactam I or Beta-Lactam II, wherein n is 0 (zero).

In other embodiments, the present invention relates to a method, composition, or use of a beta-lactam of structure Beta-Lactam I or Beta-Lactam II, wherein $R^1$ represents methyl, and $R^2$ and $R^3$ represent a hydrogen atom.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents pyridinium-yl which optionally has carbamoyl lower alkyl, carboxyl lower alkyl, or aminosulfonylamino lower alkyl at its 1-position and amino lower alkylthio at other position than the 1-position.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents pyridin-3-yl.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-carbamoylmethylpyridinium-3-yl.

In other embodiments, the present invention relates to a method, composition, or use of a beta-lactam of structure Beta-Lactam I or Beta-Lactam II, wherein $R^1$, $R^2$ and $R^3$ represent a hydrogen atom, n is 0 (zero), and Hy represents 1-carbamoylmethylpyridinium-3-yl.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-carbamoylmethyl-5-phenylpyridinium-3-yl.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents (2S)-pyrrolidin-2-yl.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-carboxymethylpyridinium-3-yl.

In other embodiments, the present invention relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-(2-aminosulfonylaminoethyl)pyridinium-3-yl.

In other embodiments, the present invention relates to a method, composition, or use wherein said beta-lactam or carbapenem corresponds to the following structure:

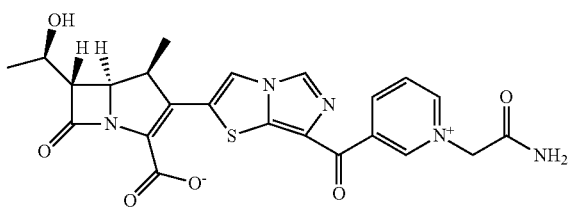 [SMILES: C[C@@H](O)[C@H]1C(=O)N2C(C(=O)[O-])=C(c3cn4cnc(C(=O)c5ccc[n+](CC(N)=O)c5)c4s3)[C@H](C)[C@H]12]

or a pharmaceutically acceptable salt, ester, or prodrug thereof. This foregoing beta-lactam or carbapenem is also known by the publicly disclosed code names ME1036 and CP5609.

Aminomethylcycline Compounds

Aminomethylcycline compounds such as 7-methylamino-9-(2,2-dimethyl-propyl)aminomethylcycline and their pharmaceutically acceptable salts, esters, and prodrugs thereof, can be used in the methods, compositions, and uses of the present invention. The compound, 7-methylamino-9-(2,2-dimethyl-propyl)aminomethylcycline, is also known by the publicly disclosed code names PTK 0796 and BAY 73-6944. See U.S. Pat. No. 6,846,939 B2, to Nelson et al., issued Jan. 25, 2005; U.S. Patent Application No. US 2005/0070510 A1, to Draper et al., published Mar. 31, 2005; U.S. Patent Application No. US 2005/0026876 A1, to Nelson et al., published Feb. 3, 2005; U.S. Patent Application No. US 2005/0026875 A1, to Nelson et al., published Feb. 3, 2005; U.S. Patent Application No. US 2004/0242548 A1, to Draper et al., published Dec. 2, 2004; U.S. Patent Application No. US 2004/0214801 A1, to Nelson et al, published Oct. 28, 2004; U.S. Patent Application No. US 2004/0214800 A1, to Levy et al., published Oct. 28, 2004; U.S. Patent Application No. US 2004/0092490 A1, to Draper et al., published May 13, 2004; U.S. Patent Application No. US 2004/0063674 A1, to Levy et al., published Apr. 1, 2004; U.S. Patent Application No. US 2003/0166585 A1, to Draper et al., published Sep. 4, 2003; U.S. Patent Application No. US 2003/0125348 A1, to Nelson et al, published Jul. 3, 2003; PCT Application No. WO 2005/009944, to Paratek Pharmaceuticals, Inc., published Feb. 3, 2005; PCT Application No. WO 2004/091513, to Paratek Pharmaceuticals, Inc., published Oct. 28, 2004; PCT Application No. WO 2004/064728, to Paratek Pharmaceuticals, Inc., published Aug. 5, 2004; PCT Application No. WO 2004/038001, to Paratek Pharmaceuticals, Inc., published May 6, 2004; PCT Application No. WO 2004/038000, to Paratek Pharmaceuticals, Inc., published May 6, 2004; PCT Application No. WO 03/075857, to Paratek Pharmaceuticals, Inc., published Sep. 18, 2003; PCT Application No. WO 03/005971, to Paratek Pharmaceuticals, Inc., published Jan. 23, 2003; PCT Application No. WO 02/072031, to Paratek Pharmaceuticals, Inc., published Sep. 19, 2002; and PCT Application No. WO 02/04406, to Trustees of Tufts College and Paratek Pharmaceuticals, Inc., published Jan. 17, 2002.

Dalbavancin

Dalbavancin and its pharmaceutically acceptable salts, esters, and prodrugs thereof, can be used in the methods, compositions, and uses of the present invention. Dalbavancin, which is a semisynthetic glycopeptide is also known by the publicly disclosed code names VER-001 and BI397. See G. Candiani et al., "In-Vitro and In-Vivo Antibacterial Activity of BI397, a New Semi-Synthetic Glycopeptide Antibiotic", J. Antimicrob. Chemotherapy, 44, pp. 179-192 (1999); U.S. Patent Application No. US 2005/0090433 A1, to Colombo et al., published Apr. 28, 2005; U.S. Patent Application No. US 2005/0004050 A1, to Stogniew, published Jan. 6, 2005; U.S. Patent Application No. US 2004/0224908 A1, to Cavaleri et al., published Nov. 11, 2004; U.S. Patent Application No. US 2004/0220122 A1, to Cavaleri et al., published Nov. 4, 2004; U.S. Patent Application No. US 2004/0198715 A1, to Cavaleri et al., published Oct. 7, 2004.

Daptomycin

Daptomycin and its pharmaceutically acceptable salts, esters, and prodrugs thereof, can be used in the methods, compositions, and uses of the present invention. Daptomycin is sold under the trade name or proprietary Cubicin. See U.S. Pat. No. 6,852,689 B2, to Oleson, Jr. et al., issued Feb. 8, 2005; U.S. Pat. No. 6,468,967 B1, to Oleson, Jr. et al., issued Oct. 22, 2002; and U.S. Pat. No. 5,912,226, to Baker et al., issued Jun. 15, 1999; and PCT Application No. WO 00/18419, to Cubist Pharmaceuticals, Inc., published Apr. 6, 2000.

Oritavancin

Oritavancin and its pharmaceutically acceptable salts, esters, and prodrugs thereof, can be used in the methods, compositions, and uses of the present invention. Oritavancin, which is a glycopeptide, is also known by the publicly disclosed code name LY333328. See R. C. Mercier et al., "Pharmacodynamic Evaluation of a New Glycopeptide, LY333328, and In Vitro Activity against *Staphylococcus aureus* and *Enterococcus faecium*", Antimicrobial Agents and Chemotherapy, vol. 41, no. 6, pp. 1307-1312 (June 1997); U.S. Pat. No. 5,998,581, to Berglund et al., issued Dec. 7, 1999 and its certificate of correction of Nov. 14, 2000; U.S. Pat. No. 5,994,297, to Nicas et al., issued Nov. 30, 1999; U.S. Pat. No. 5,977,062, to Cooper et al., issued Nov. 2, 1999; U.S. Pat. No. 5,952,466, to Berglund et al, issued Sep. 14, 1999; U.S. Pat. No. 5,939,382, to Berglund et al., issued Aug. 17, 1999; U.S. Pat. No. 5,843,889, to Cooper et al., issued Dec. 1, 1998 and its certificate of correction of Mar. 28, 2000; U.S. Pat. No. 5,840,684, to Cooper et al., issued Nov. 24, 1998; PCT Application No. WO 00/66144, to Eli Lilly and Company, published Nov. 9, 2000; PCT Application No. WO 99/10006, to Eli Lilly and Company, published Mar. 4, 1999; PCT Application No. WO 98/22121, to Eli Lilly and Company, published May 28, 1998; PCT Application No. WO 98/21952, to Eli Lilly and Company, published May 28, 1998; and PCT Application No. WO 96/30401, to Eli Lilly and Company, published Oct. 3, 1996.

Televancin

Televancin and its pharmaceutically acceptable salts, esters, and prodrugs thereof, can be used in the methods, compositions, and uses of the present invention. Televancin, which is a peptidoglycan, can be prepared by the sequential reduction amination of vancomycin and reaction with aminomethylphosphonic acid. Televancin can also be prepared by the reductive alkylation of vancomycin with N-decyl-N-fluoroenyl-methyloxycarbonyl-2-aminoacetaldehyde via sodium cyano-borohydride and trifluoroacetic acid, and modification of the resorcinol position via Mannich aminomethylation. Televancin can also be prepared from vancomycin or its analogues by the sequential reaction with a protected amino-aldehyde, an amine and then an aminoalkylphosphonic acid in the presence of formaldehyde. See U.S. Pat. No. 6,887,976 B2, to Leadbetter et al., issued May 3, 2005; U.S. Pat. No. 6,878,686 B2, to Marquess et al., issued Apr. 12, 2005; U.S. Pat. No. 6,872,804 B2, to Mu, issued Mar. 29, 2005; U.S. Pat. No. 6,872,701 B2, to Leadbetter et al., issued Mar. 29, 2005; U.S. Pat. No. 6,858,584 B2, to Judice et al., issued Feb. 22, 2005; U.S. Pat. No. 6,831,150 B2, to Linsell, issued Dec. 14, 2004; U.S. Pat. No. 6,828,299 B2, to Yang et al., issued Dec. 7, 2004; U.S. Pat. No. 6,770,621 B2, to Linsell et al., issued Aug. 3, 2004; U.S. Pat. No. 6,635,618 B2, to Leadbetter et al., issued Oct. 21, 2003; U.S. Pat. No. 6,620, 781 B2, to Linsell et al., issued Sep. 16, 2003; U.S. Pat. No. 6,518,242 B1, to Chen et al. issued Feb. 11, 2003; and U.S. Pat. No. 6,455,669 B1, to Judice et al., issued Sep. 24, 2002; and PCT Application No. WO 03/029270, to Theravance, Inc., published Apr. 10, 2003.

DK-507k

The compound DK-507k and its pharmaceutically acceptable salts, esters, and prodrugs thereof, can be used in the methods, compositions, and uses of the present invention. DK-507k can be described as a fluoroquinolone. DK-507k is also known by the chemical name (–)-7-[(7S)-7-amino-5-azaspiro[2.4]heptan-5-yl]-6-fluoro-1-[(1R,2S)-2-fluoro-1-cyclopropyl]-1,4-dihydro-8-methoxy-4-oxo-3-quinolinecarboxylic acid monohydrochloride monohydrate. See Otani et al., *In Vitro and In Vivo antibacterial Activities of DK-507k, a Novel Fluoroquinolone*, Antimicrobial Agents and Chemotherapy, Vol. 47, no. 12, pages 3750-3759 (2003); Japanese Patent No. JP 2004244380 A2, to Daiichi Seiyaku Co., Ltd., Japan, Sep. 2, 2004; PCT Application No. WO 2004/058261, to Daiichi Pharmaceutical Co., Ltd., Japan, published Jul. 15, 2004; PCT Patent Application No., WO 2003/076248, to Daiichi PHarmaceuitcal Co., Ltd., Japan, published Sep. 18, 2003; Japanese Patent No. JP 2003096075 A2. to Daiichi Seiyaku Co., Ltd., Japan, Apr. 3, 2003; Japanese Patent No. JP 2002255962 A2, to Daiichi Seiyaku Co., Ltd., Japan, Sep. 11, 2002; Japanese Patent No. JP 2002201191 A2 to Daiichi Seiyaku Co., Ltd., Japan, Jul. 16, 2002; PCT Application No. WO 2001/072738, to Daiichi Pharmaceutical Co., Ltd., Japan, published Oct. 4, 2001; U.S. Pat. No. 6,900,225 B2, to Takemura et al., issued May 31, 2005; U.S. Patent Application No. 2004/142957 A1, to Takemura et al., published Jul. 22, 2004; U.S. Patent Application No. 2003/187008 A1, to Takemura et al., published Oct. 2, 2003; PCT Application No. WO 2001/058876, to Daiichi Pharmaceutical Co., Ltd., Japan, published Aug. 16, 2001; and U.S. Patent Application No. 2003/119848 A1, to Takemura et al., published Jun. 26, 2003.

DK-507k can be represented by the following formula;

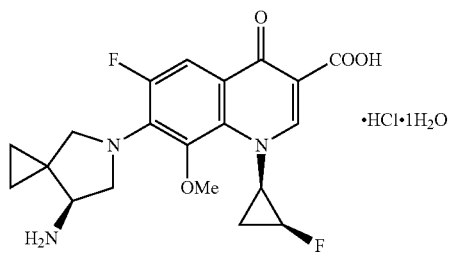 [SMILES: COc1c(N2C[C@@H](N)C3(CC3)C2)c(F)cc2c(=O)c(C(=O)O)cn([C@@H]3C[C@@H]3F)c12]

The compound can also be obtained as crystals exhibiting characteristic peaks in the vicinity of angles of diffraction (2θ) of 6.9, 10.5, 14.4, 23.1, 26.9, and 27.8(°) when subjected to powder X-ray diffractometry.

The anhydrous free acid of the above compound, as well as other salts, esters, and prodrugs, and also hydrates of the compounds can be prepared and used in the present invention. Also other crystal forms of the foregoing can be prepared and used in the present invention.

The dose of the pharmaceutical active and mode of administration of the pharmaceutical composition will depend upon the intended patient or subject and the targeted microorganism, e.g., the target bacterial organism.

As further described below, it is often advantageous to mill the pharmaceutical active to a small and uniform particle size, usually in the micron range, i.e. micronization. Milling can be performed using standard techniques well known to one of ordinary skill in the art. Useful particle size ranges for the pharmaceutical active are generally from about 0.25 microns to about 100 microns, preferably from about 0.5 microns to about 50 microns, and even more preferably from about 1 micron to about 10 microns.

4. METHODS OF MAKING THE PHARMACEUTICAL CARRIERS AND PHARMACEUTICALS COMPOSITIONS

Useful carriers and compositions for oral administration can be prepared by any of the methods well known in the pharmaceutical art, described, for example, in Eds. R. C. Rowe, et al., Handbook of Pharmaceutical Excipients, Fifth Edition, Pharmaceutical Press (2006), *Remington Pharmaceutical Sciences*, 18th ed. (Mack Publishing Company, 1990), *Remington: The Science and Practice of Pharmacy*, 20th Edition, Baltimore, Md.: Lippincott Williams & Wilkins, 2000, and L. Lachman, H. A. Lieberman, J. L. Kanig (1986). *The Theory and Practice of Industrial Pharmacy* (3rd Ed.). Lea & Febiger, Philadelphia, which are incorporated by reference herein in their entirety.

Formulations of the present invention suitable for oral administration can be in the form of: discrete units such as tablets, capsules, capsules (e.g., soft and hard and gelatin capsules and hard starch capsules), sachets, troches, lozenges, or other forms each containing a predetermined amount of the drug.

Oral compositions can be formulated in dosage unit form for ease of administration and uniformity of dosage. Dosage unit form refers to physically discrete units suited as unitary dosages for the subject to be treated; each unit containing a predetermined quantity of pharmaceutical active compound calculated to produce the desired therapeutic effect in association with the required pharmaceutical carrier. The specification for the dosage unit forms of the invention are dictated by and directly dependent on the unique characteristics of the active compound and the therapeutic effect to be achieved, and the limitations inherent in the art of compounding such an active compound for the treatment of individuals.

Tablets

The tablets herein are made using any of the standard mixing and manufacturing techniques. The tablets can be made via either wet granulation or direct dry compression. Generally, the tablets have an intragranular component comprising the pharmaceutical active, wherein these granules are further combined with additional excipients, i.e. extragranular components to form the finished tablets. The tablets can be further coated.

Soft Gelatin Capsules

The pharmaceutical compositions of the present invention can also be encapsulated in a soft gelatin shell. Optionally, the soft gelatin shell is essentially transparent so as to enhance the aesthetic qualities of the capsule. The soft gelatin shells comprise the following essential, as well as optional, components.

Gelatin is an essential component of the soft gelatin shells of the instant invention. The starting gelatin material used in the manufacture of soft capsules is obtained by the partial hydrolysis of collagenous material, such as the skin, white connective tissues, or bones of animals. Gelatin material can be classified as Type A gelatin, which is obtained from the acid-processing of porcine skins and exhibits an isoelectric point between pH 7 and pH 9; and Type B gelatin, which is obtained from the alkaline-processing of bone and animal (bovine) skins and exhibits an isoelectric point between pH 4.7 and pH 5.2. Blends of Type A and Type B gelatins can be used to obtain a gelatin with the requisite viscosity and bloom strength characteristics for capsule manufacture. Gelatin suitable for capsule manufacture is commercially available from the Sigma Chemical Company, St. Louis, Mo. For a general description of gelatin and gelatin-based capsules, see Remingtons's Pharmaceutical Sciences, 16th ed., Mack Publishing Company, Easton, Pa. (1980), page 1245 and pages 1576-1582; and U.S. Pat. No. 4,935,243, to Borkan et al., issued Jun. 19, 1990; these two references being incorporated herein by reference in their entirety.

The soft gelatin shell of the capsules of the instant invention, as initially prepared, comprises from about 20% to about 60% gelatin, more preferably from about 25% to about 50% gelatin, and most preferably from about 40% to about 50% gelatin. The gelatin can be of Type A, Type B, or a mixture thereof with bloom numbers ranging from about 60 to about 300.

A plasticizer is another essential component of the soft gelatin shells of the instant invention. One or more plasticizers is incorporated to produce a soft gelatin shell. The soft gelatin thus obtained has the required flexibility characteristics for use as an encapsulation agent. Useful plasticizers of the present invention include glycerin, sorbitan, sorbitol, or similar low molecular weight polyols, and mixtures thereof.

The shell of the present invention, as initially prepared, comprises from about 10% to about 35% plasticizer, preferably from about 10% to about 25% plasticizer, and most preferably from about 10% to about 20% plasticizer. A preferred plasticizer useful in the present invention is glycerin.

The soft gelatin shells of the instant invention also comprise water as an essential component. Without being limited by theory, the water is believed to aid in the rapid dissolution or rupture of the soft gelatin shell upon contact with the gastrointestinal fluids encountered in the body.

The shell of the present invention, as initially prepared, comprises from about 15% to about 50% water, more preferably from about 25% to about 40% water, and most preferably from about 30% to about 40% water.

Other optional components which can be incorporated into the soft gelatin shells include colorings, flavorings, preservatives, anti-oxidants, essences, and other aesthetically pleasing components.

The solubilized pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, and any optional components in a suitable vessel and agitating and/or stirring while heating to about 65° C. until a uniform. solution is obtained. This soft gelatin shell preparation can then be used for encapsulating the desired quantity of the solubilized fill composition employing standard encapsulation methodology to produce one-piece, hermetically-sealed, soft gelatin capsules. The gelatin capsules are formed into the desired shape and size so that they can be readily swallowed. The soft gelatin capsules of the instant invention are of a suitable size for easy swallowing and typically contain from about 100 mg to about 2000 mg of the Pharmaceutical active composition. Soft gelatin capsules and encapsulation methods are described in P. K. Wilkinson et al., "Softgels: Manufacturing Considerations", Drugs and the Pharmaceutical Sciences, 41 (Specialized Drug Delivery Systems), P. Tyle, Ed. (Marcel Dekker, Inc., New York, 1990) pp. 409-449; F. S. Horn et al., "Capsules, Soft" Encyclopedia of Pharmaceutical Technology, vol. 2, J. Swarbrick and J. C. Boylan, eds. (Marcel Dekker, Inc., New York, 1990) pp. 269-284; M. S. Patel et al., "Advances in Softgel Formulation Technology", Manufacturing Chemist, vol. 60, no. 7, pp. 26-28 (July 1989); M. S. Patel et al., "Softgel Technology", Manufacturing Chemist, vol. 60, no. 8, pp. 47-49 (August 1989); R. F. Jimerson, "Softgel (Soft Gelatin Capsule) Update", Drug Development and Industrial Pharmacy (Interphex '86 Conference), vol. 12, no. 8 & 9, pp. 1133-1144 (1986); and W. R. Ebert, "Soft Elastic Gelatin Capsules: A Unique Dosage Form", Pharmaceutical Technology, vol. 1, no. 5, pp. 44-50 (1977); these references are incorporated by reference herein in their entirety. The resulting soft gelatin capsule is soluble in water and in gastrointestinal fluids. Upon swallowing the capsule, the gelatin shell rapidly dissolves or ruptures in the gastrointestinal tract thereby introducing the pharmaceutical actives into the physiological system.

Hard Capsules

In still another embodiment the unit dosage form is a hard capsule (i.e. a starch or gelatin hard capsule), for example a starch capsule such as Capill, from Capsulgel (Greenwood, S.C.) The capsule can be filled with the pharmaceutical compositions of the present invention.

5. METHODS OF TREATING, PREVENTING OR REDUCING THE RISK OF MICROBIAL INFECTIONS

The present invention also provides a method of treating, preventing, or reducing the risk of a microbial infection in a patient or subject. These methods comprise administering a pharmaceutically or prophylactically effective amount of the pharmaceutical actives of the present invention as a pharmaceutical composition or formulation from the carriers of the present invention to a patient or subject at an appropriate dosage.

One of ordinary skill in the art can select an appropriate dosage of the pharmaceutical active. In practicing the methods of the present invention, it is desired that the blood and or tissue level in the patient or subject of the compound be of an appropriate level for a sufficient time interval. As mentioned above, to provide therapeutic efficacy, it is generally desired that the antimicrobial agent be administered to the patient to achieve systemic concentrations in the bloodstream or target organs above a minimum inhibitory concentration (i.e. the MIC) and for a sufficient time against the particular microbial organism or organisms being targeted.

The pharmaceutical compositions of the present invention are useful for treating, preventing, or reducing the risk of a disorder such as a microbial infection in a patient or subject, e.g., a human, or a nonhuman mammal or other animal. This comprises the step or steps of administering a pharmaceutically effective or prophylactically effective amount of a composition of the present invention. Microbial infections or treatments include, inter alia, those selected from the group consisting of a skin infection, pneumonia (both nosocomial and community acquired pneumonia), post-viral pneumonia, an abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant Enterococci infection, a linezolid-resistant organism infection, and tuberculosis.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of the pharmaceutical active will be in the range of from about 0.1 to about 100 mg/kg of body weight/day, more preferably from about 1.0 to about 50 mg/kg of body weight/day. The amount administered will also likely depend on such variables as the disease or condition that one is intending to treat, prevent, or reduce the risk of, the overall health status of the patient, the relative biological efficacy of the parent compound delivered from the hydrogen sulfate salt, the formulation, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

6. EXAMPLES

Tablets

Tablets compositions are made using standard mixing techniques. Both wet and dry granulation methods can be used. The tablets useful herein can have both intragranular as well as extragranular components, and some of the same components can be used both in the intragranular and extra-granular portions of the table. The tablets can be further coated with waxes, gelatins, shellacs, and other suitable materials, and can be imprinted or polished. All components in the following tables are on a weight basis of mg, unless otherwise indicated.

TABLE 1

Tablet Examples 1-5

|  | Tablet 1 | Tablet 2 | Tablet 3 | Tablet 4 | Tablet 5 |
|---|---|---|---|---|---|
| Drug active[1] | 541.6 | 541.6 | 541.6 | 541.6 | 541.6 |
| Emulsifier | 70.00[2] | 70.00[3] | 115.00[2] | 75.00[3] | 85.00[2] |
| Hydroxypropyl-methylcellulose | 45.00 | 45.00 | — | 45.00 | — |
| Sodium starch glycolate | 45.00 | 45.00 | 45.00 | 45.00 | 45.00 |
| Mannitol | 54.40 | 54.40 | 54.40 | 54.40 | 54.40 |
| Microcrystalline cellulose | 32.00 | 32.00 | 32.00 | 32.00 | 32.00 |
| Fumed silica | 8.00 | 8.00 | 8.00 | 8.00 | 8.00 |
| Magnesium stearate | 4.00 | 4.00 | 4.00 | 4.00 | 4.00 |

[1]N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2]Gelucire 50/13
[3]Gelucire 44/14

The foregoing tablets are useful for administering to a patient or subject to treat, prevent, or reduce the risk of a microbial infection.

TABLE 2

Tablet Examples 6-10

|  | Tablet 6 | Tablet 7 | Tablet 8 | Tablet 9 | Tablet 10 |
|---|---|---|---|---|---|
| Drug active[1] | 541.6 | 541.6 | 541.6 | 541.6 | 541.6 |
| Emulsifier | 70.00[2] | 70.00[3] | 80.00[2] | 65.00[3] | 110.00[3] |
| Hydroxypropyl-methylcellulose | 35.00 | 35.00 | — | 45.00 | — |
| Sodium starch glycolate | 35.00 | 35.00 | 35.00 | 45.00 | 50.00 |
| Mannitol | 54.40 | 54.40 | 54.40 | 54.40 | 54.40 |
| Microcrystalline cellulose | 32.00 | 32.00 | 32.00 | 32.00 | 32.00 |
| Fumed silica | 8.00 | 8.00 | 8.00 | 8.00 | 8.00 |
| Magnesium stearate | 4.00 | 4.00 | 4.00 | 4.00 | 4.00 |

[1]N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2]Gelucire 50/13
[3]Gelucire 44/14

The foregoing tablets are useful for administering to a patient or subject to treat, prevent, or reduce the risk of a microbial infection.

TABLE 3

Tablet Examples 11-15

|  | Tablet 11 | Tablet 12 | Tablet 13 | Tablet 14 | Tablet 15 |
|---|---|---|---|---|---|
| Drug active[1] | 541.6 | 541.6 | 541.1 | 541.6 | 541.1 |
| Emulsifier | 80.00[2] | 80.00[3] | 120.00[2] | 85.00[3] | 90.00[2] |
| Hydroxypropyl-methylcellulose | 40.00 | 40.00 | — | 40.00 | — |
| Sodium starch glycolate | 40.00 | 40.00 | 40.00 | 40.00 | 40.00 |
| Mannitol | 54.40 | 54.40 | 54.40 | 54.40 | 54.40 |
| Microcrystalline cellulose | 32.00 | 32.00 | 32.00 | 32.00 | 32.00 |
| Fumed silica | 8.00 | 8.00 | 8.00 | 8.00 | 8.00 |
| Magnesium stearate | 4.00 | 4.00 | 4.00 | 4.00 | 4.00 |

[1]N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2]Gelucire 50/13
[3]Gelucire 44/14

The foregoing tablets are useful for administering to a patient or subject to treat, prevent, or reduce the risk of a microbial infection.

TABLE 4

Tablet Examples 16-20

|  | Tablet 16 | Tablet 17 | Tablet 18 | Tablet 19 | Tablet 20 |
|---|---|---|---|---|---|
| Drug active[1] | 541.6 | 541.6 | 541.1 | 541.6 | 541.1 |
| Emulsifier | 60.00[2] | 60.00[3] | 75.00[2] | 75.00[3] | 120.00[3] |
| Hydroxypropyl-methylcellulose | 40.00 | 40.00 | — | 40.00 | — |
| Sodium starch glycolate | 40.00 | 40.00 | 40.00 | 40.00 | 40.00 |
| Mannitol | 54.40 | 54.40 | 54.40 | 54.40 | 54.40 |
| Microcrystalline cellulose | 32.00 | 32.00 | 32.00 | 32.00 | 32.00 |
| Fumed silica | 8.00 | 8.00 | 8.00 | 8.00 | 8.00 |
| Magnesium stearate | 4.00 | 4.00 | 4.00 | 4.00 | 4.00 |

[1]N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2]Gelucire 50/13
[3]Gelucire 44/14

The foregoing tablets are useful for administering to a patient or subject to treat, prevent, or reduce the risk of a microbial infection.

Capsules

The capsule compositions are made using standard mixing techniques. Both wet and dry granulation methods can be used to make the granulation component which is then loaded into a gelatin capsule, such as a soft gelatin capsule or a hard two piece gelatin or starch capsule. All components are on a weight basis of mg per capsule.

TABLE 5

Capsule Examples 1-5

| | Capsule 1 | Capsule 2 | Capsule 3 | Capsule 4 | Capsule 5 |
|---|---|---|---|---|---|
| Drug active[1] | 324.93 | 324.93 | 324.93 | 324.93 | 324.93 |
| Emulsifier | 65.00[2] | 125.00[2] | 65.00[2] | 65.00[2] | 65.00[2] |
| Povidone | — | — | 25.00 | 20.00 | 55.00 |
| Hydroxypropyl-methylcellulose | 31.00 | — | — | 15.00 | — |
| Sodium starch glycolate | 30.00 | 25.00 | 30.00 | 30.00 | 30.00 |
| Mannitol | 78.00 | 66.00 | 78.00 | 78.00 | 63.00 |
| Microcrystalline cellulose | 58.57 | 46.57 | 64.57 | 64.57 | 49.57 |
| Fumed silica | 8.00 | 8.00 | 8.00 | 8.00 | 8.00 |
| Magnesium stearate | 4.50 | 4.50 | 4.50 | 4.50 | 4.50 |

[1] N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2] Gelucire 44/14

The foregoing capsules are useful for administering to a patient or subject to treat, prevent, or reduce the risk of a microbial infection.

TABLE 6

Capsule Examples 6-10

| | Capsule 6 | Capsule 7 | Capsule 8 | Capsule 9 | Capsule 10 |
|---|---|---|---|---|---|
| Drug active[1] | 324.93 | 324.93 | 324.93 | 324.93 | 324.93 |
| Emulsifier | 55.00[2] | 55.00[3] | 115.00[3] | 55.00[3] | 55.00[3] |
| Povidone | 30.00 | — | — | 35.00 | 15.00 |
| Hydroxypropyl-methylcellulose | — | 36.00 | — | — | 20.00 |
| Sodium starch glycolate | 35.00 | 35.00 | 35.00 | 30.00 | 30.00 |
| Mannitol | 78.00 | 78.00 | 66.00 | 78.00 | 78.00 |
| Microcrystalline cellulose | 64.57 | 58.57 | 46.57 | 64.57 | 64.57 |
| Fumed silica | 8.00 | 8.00 | 8.00 | 8.00 | 8.00 |
| Magnesium stearate | 4.50 | 4.50 | 4.50 | 4.50 | 4.50 |

[1] N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2] Gelucire 44/14
[3] Gelucire 50/13

The foregoing capsules are useful for administering to a patient or subject to treat, prevent, or reduce the risk of a microbial infection.

TABLE 7

Capsule Examples 11-15

| | Capsule 11 | Capsule 12 | Capsule 13 | Capsule 14 | Capsule 15 |
|---|---|---|---|---|---|
| Drug active[1] | 324.93 | 324.93 | 324.93 | 324.93 | 324.93 |
| Emulsifier | 60.00[2] | 120.00[2] | 60.00[2] | 60.00[2] | 60.00[2] |
| Povidone | — | — | 30.00 | 15.00 | 60.00 |
| Hydroxypropyl-methylcellulose | 36.00 | — | — | 15.00 | — |
| Sodium starch glycolate | 30.00 | 30.00 | 30.00 | 30.00 | 30.00 |
| Mannitol | 78.00 | 66.00 | 78.00 | 78.00 | 63.00 |
| Microcrystalline cellulose | 58.57 | 46.57 | 64.57 | 64.57 | 49.57 |

TABLE 7-continued

Capsule Examples 11-15

| | Capsule 11 | Capsule 12 | Capsule 13 | Capsule 14 | Capsule 15 |
|---|---|---|---|---|---|
| Fumed silica | 8.00 | 8.00 | 8.00 | 8.00 | 8.00 |
| Magnesium stearate | 4.50 | 4.50 | 4.50 | 4.50 | 4.50 |

[1] N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2] Gelucire 44/14

The foregoing capsules are useful for administering to a patient or subject to treat, prevent, or reduce the risk of a microbial infection.

TABLE 8

Capsule Examples 16-20

| | Capsule 16 | Capsule 17 | Capsule 18 | Capsule 19 | Capsule 20 |
|---|---|---|---|---|---|
| Drug active[1] | 324.93 | 324.93 | 324.93 | 324.93 | 324.93 |
| Emulsifier | 60.00[2] | 60.00[3] | 120.00[3] | 60.00[3] | 60.00[3] |
| Povidone | 30.00 | — | — | 30.00 | 15.00 |
| Hydroxypropyl-methylcellulose | — | 36.00 | — | — | 15.00 |
| Sodium starch glycolate | 30.00 | 30.00 | 30.00 | 30.00 | 30.00 |
| Mannitol | 78.00 | 78.00 | 66.00 | 78.00 | 78.00 |
| Microcrystalline cellulose | 64.57 | 58.57 | 46.57 | 64.57 | 64.57 |
| Fumed silica | 8.00 | 8.00 | 8.00 | 8.00 | 8.00 |
| Magnesium stearate | 4.50 | 4.50 | 4.50 | 4.50 | 4.50 |

[1] N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt
[2] Gelucire 44/14
[3] Gelucire 50/13

The foregoing capsules are useful for administering to a patient or subject to treat, prevent, or reduce the risk of a microbial infection.

Soft Gelatin Capsules

A soft gelatin mixture is first prepared from the following ingredients.

| Ingredient | Weight % |
|---|---|
| Gelatin | 47.00 |
| Glycerin | 15.00 |
| Water | QS 100 |

The above ingredients are combined in a suitable vessel and heated with mixing at about 65.degrees C. to form a uniform solution. Using standard encapsulation methodology, the resulting solution is used to prepare soft gelatin capsules containing approximately 600 mg of the compositions of Capsules 1 to 20, above. The resulting soft gelatin capsules are suitable for oral administration.

Hard Gelatin Capsules

Hard gelatin capsules are purchased from any commercially available source. The capsules are filled manually or by capsule filling machine with approximately 600 mg of the compositions of Capsule 1 to 20 above. The resulting hard gelatin capsules are suitable for oral administration.

TABLE 9

Solid Oral Formulation Composition Example 1

| | Solid Oral Formulation |
|---|---|
| Drug active[1] | 162.5[1] |
| Fumaric acid | 75.00 |
| Tartaric acid | 75.00 |
| Sodium Starch Glycolate | 0-25.00 |
| Polydextrose | 25.00 |
| Gelucire 44/14 | 25-50.00 |
| Cyclodextrin (cavitron hydroxypropyl-β-cyclodextrin) | 0-125.00 |
| Mannitol | 50-100 |
| Purified water[2] | |
| Colloidal silicon dioxide | 4.00 |
| Magnesium stearate | 3.50 |
| Enteric film coating | 0-100 |

[1]N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide monohydrochloride salt. Note that 162.5 mg isequivalent to 150 mg of the free base.
[2]Purified water is used as a granulating agent and is removed during the drying process.

The above ingredients are combined using standard wet granulation procedures to form tablets, which are then optionally enteric coated. The resulting compositions are suitable for oral administration.

Example

Dissolution Testing in a Simulated Gastrointestinal System

A. To Develop an Easy-to-Use 2-Step Dissolution Method Simulating Gastrointestinal Systems.

The common ion effect was studied using dissolution and microscopic methods. The microscopic method was conducted with drug suspended in water, pH 1.2, pH 4 and pH 6.5 buffers with and without sodium chloride. The dissolution of the drug and its granulations were studied using three different 2-step dissolution methods which entails the following: Method #1: simple 2-step buffers at pH 4 from 0-30 minutes and at pH 6.5 from 30-90 minutes. Method #2: simple 2-step buffers with the presence of chloride ion in both steps. Method #3: simple buffer at pH 4 with presence of chloride ion from 0-30 minutes; and buffer with bile salts and surfactants at pH 6.5 from 30-90 minutes. The two steps represent fed stomach and intestinal conditions, respectively.

The microscopy indicated that the drug formed aggregates in the presence of chloride ion. Unexpectedly, the alternative non-chloride salt (neat drug) flocculated into larger aggregates. Thus dissolution methods addressing both common ion effects and gastrointestinal conditions were studied. The results indicated that the simple buffer in the presence of chloride ion was the most discriminating dissolution medium. For the same formulations, the dissolution rates were in the following order: 2-step simple buffer without sodium chloride>2-step with bile-salts and surfactants>simple buffer with sodium chloride. Using the simple buffer system with sodium chloride enabled screen formulations to achieve the most super-saturation with a reduced common ion effect. The simple buffer system without chloride ion, on the other hand, did not provide enough power to discriminate the formulations of a drug with a low chloride Ksp.

2-Step dissolution using simple buffer with sodium chloride present is an easy-to-use surrogate for the conventional 2-step dissolution system with bile-salts and surfactants. The dissolution in such medium enables the study of super-saturation and common ion effects for formulations of high dose hydrochloride salt drugs with sub-microgram water solubility.

B. Formulation Approaches to Achieve Super-Saturation

Investigate formulation approaches to overcome poor water solubility, common ion effect, and obtain super-saturation for a drug with sub-microgram solubility.

Drug compound was granulated with various mixtures of excipients. The drug substances and the granulations were studied using 2-step dissolution methods at pH 4 from 0 to 30 minutes and at pH 6.5 from 30 to 90 minutes in the presence and absence of sodium chloride.

The dissolution data, conducted in gastrointestinal representative system, indicated that the pH modifier with a relative lower solubility improved dissolution to a greater extend than a pH modifier with a higher solubility. The data also indicated that certain surfactants and polymers selected for the formulation further enhanced supersaturation and reduced the common ion effect from chloride. Usage of common water soluble excipients in the formulation facilitated the dissolution in addition to manufacturability. Even though the alternative non-chloride salt has significantly increased solubility at acidic medium, the dissolution of neat non-chloride salt is similar to that of chloride salt. The microscopy showed that the non-chloride salt formed aggregates in the presence of chloride ion. However, once formulated with selected excipients, the advantage of non-chloride salt is shown in dissolution.

Dissolution and bioavailability of a basic drug with poor solubility can be enhanced by using selected pH modifying agents, surfactants, and polymers. The alternative salts, when formulated with the optimized excipients, can also increase dissolution. Selecting a dissolution method which addresses both gastrointestinal system and the common ion effect is critical to select formulations for maximum exposure.

C. Studies on 2-Step Dissolution Testing of a Drug in Simulated Gastrointestinal System To develop a simple 2-step dissolution method to screen formulations aimed to provide supersaturation To examine the effects of sodium chloride on dissolution of a hydrochloride salt of a water insoluble drug To discriminate formulations under fed GI pH conditions To study in-vivo in-vitro correlation of the dissolution system.

Traditional 2-step dissolution systems use bile salts and surfactant that is time consuming to use and sometimes not discriminating enough for formulation screening The goal is to develop a easy to use 2-step dissolution method, which simulates gastrointestinal pH values and the common ion effect without using bile salt and surfactant.

It is well known that hydrochloride salt of a water insoluble compound presents common ion effect. Thus, sodium chloride was added in the dissolution buffer to simulate common ion effect.

A hydrochloride salt of a water insoluble drug was selected as a model compound, which has following biophainiaceutical properties:
 pKa=6.8 and 9.4;
 log P=0.7;
 Intrinsic solubility=0.01 mg/ml at pH 6.8;
 Solubility of salt in water:
  2.6, 0.2, and 0.06 mg/ml at pH 4, 5.4 and 6.5, resp.
 Caco-2 permeability=$0.5 \times 10^{-6}$ cm/s;
 Monkey oral bioavailability=15% at 20 mg/kg dose
 Positive food effect (4×).

TABLE 10 pH of Gastrointestine System and that of Dissolution Medium

| | Stomach pH | Intestine pH |
|---|---|---|
| Fast | pH 1.7<br>BC: 7-18 mM/pH | pH 6.2<br>BC: 5.6 mM/pH |
| Fed | pH 4 (ave): 6.4 (im.) to 2.7 (3.5 hrs)<br>BC: 14-28 mM/pH | pH 5.4 for 4 hrs<br>BC: 18-30 mM/pH |

Source: Dressman: Pharmaceutical Research, p 165-176, vol 23, No. 1, January 2006
BC = buffer capacity Formulation Preparation Bulk drug powders were wet granulated with and without excipients. Granules were dried and sized through a #18 mesh screen.

Polarized Microscopic Observation

Microscopic test was conducted with drug suspended in water, pH 1.2, 4, and 6.5 buffers with and without sodium chloride.

Dissolution Test:

Four dissolution media were tested. Results of these tests are shown in line-graph formats in FIGS. 3-7. Bulk drug powders were wet granulated with and without excipients. Granules were dried and sized through a No. 18 mesh screen. Dissolution of the drug and its granulations were studied using four different 2-step dissolution methods. Method 1: 2-step dissolution test with the first dissolution step involves a buffer at pH 4.0 for 0-30 minutes, and the second dissolution step involves a buffer at pH 5.4 for 30-90 minutes (bottom right hand panel). Method 2: 2-step dissolution test with the first dissolution step involves a buffer at pH 4.0 for 0-30 minutes, and the second dissolution step involves a buffer at pH 6.5 for 30-90 minutes (upper right panel). Method 3: 2-step dissolution test of Method 2, but buffers in both the steps comprise chloride ion. Method 4: 2-step dissolution test of Method 2, but here the first dissolution step involves a buffer at pH 4.0 with chloride ion for 0-30 minutes; and second dissolution step involves a buffer at pH 6.5 with chloride ion, bile salts and surfactants for 30-90 mins. The two steps represent fed stomach and intestinal conditions respectively. Intestine pH (literature) indicates published conditions in Dressman, *Pharmaceutical Research*, 23(1):165-176 (2006) (as shown in Table 10). These four methods are listed below in Table 11.

TABLE 11

The Four 2-Step Dissolution Methods Tested (results shown in FIGS. 3-7).

| # | 0-30 minutes | 30-90 minutes |
|---|---|---|
| 1 | pH 4 acetate buffer<br>(100 mM) | pH 5.4<br>(add pH 6.4 phosphate buffer, 50 mM) |
| 2 | pH 4 acetate buffer<br>(100 mM) | pH 6.5<br>(add pH 7.0 phosphate buffer, 50 mM) |
| 3 | pH 4 acetate buffer<br>(100 mM) + 0.9% NaCl | pH 6.5 + 0.9% NaCl<br>(add pH 7.0 phosphate buffer (50 mM) |
| 4 | pH 4 acetate buffer<br>(100 mM) + 0.9% NaCl | pH 6.5 + KCl + Taurocholate, and lecithin<br>(add phosphate buffer, 50 mM with potassium chloride, taurocholate, and lecithin) |

Figure 3:
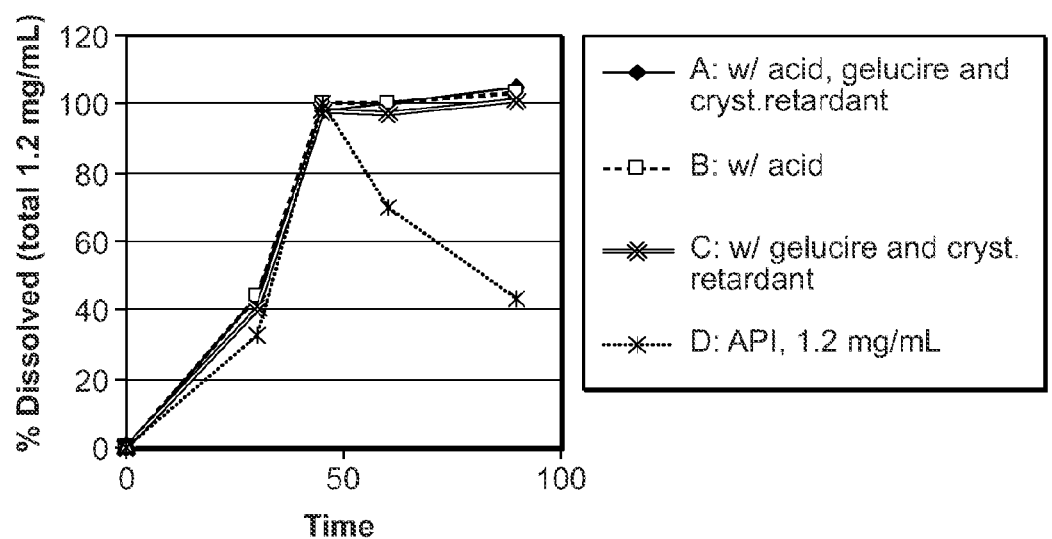
FIG. 3 depicts the results of the 2-step dissolution test performed following Method 1. Dissolution of RX-Drug was tested in a buffer at pH 4.0 for 0-30 minutes and then after transferring to a buffer at pH 5.4 for 30-90 minutes.

The results of the study are shown in FIGS. 3-7. FIG. 3 depicts the results of the 2-step dissolution test performed following Method 1 described in Table 11 (see above). Dissolution of RX-Drug was tested in a buffer at pH 4.0 for 0-30 minutes and then after transferring to a buffer at pH 5.4 for 30-90 minutes. The two conditions did not distinguish the formulations (A-C) except for drug substance (not shown).

Figure 4:
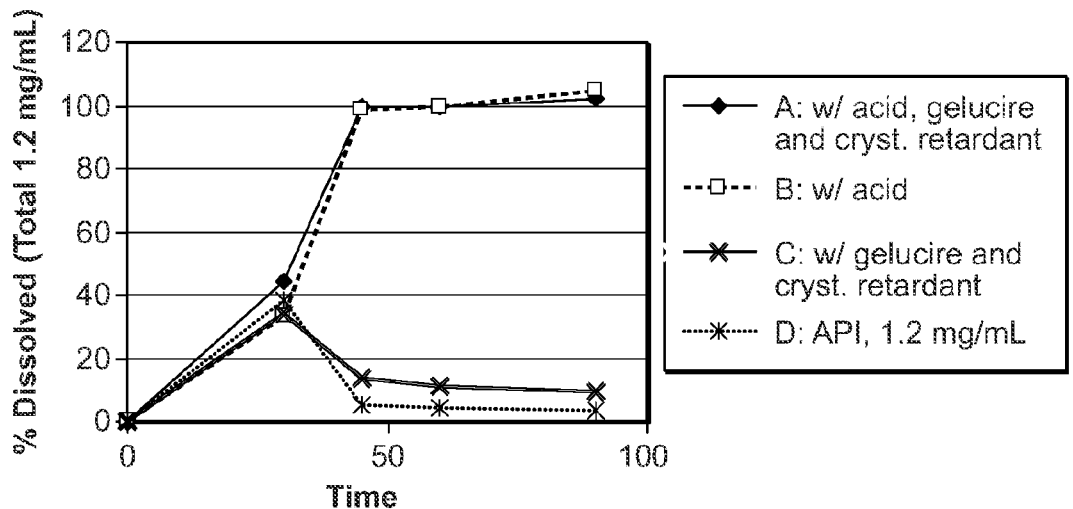
FIG. 4 depicts the results of the 2-step dissolution test performed following Method 2. Dissolution of RX-Drug was tested in a buffer at pH 4.0 for 0-30 minutes and then after transferring to a buffer at pH 6.5 for 30-90 minutes.

FIG. 4 depicts the results of the 2-step dissolution test performed following Method 2 described in Table 11 (see above). Dissolution of RX-Drug was tested in a buffer at pH 4.0 for 0-30 minutes and then after transferring to a buffer at pH 6.5 for 30-90 minutes. The percent dissolved from the formulations A and B with acidifier reached 6-8 time higher than the control. But the dissolution did not address the common ion effect, and it did not distinguish acidified formulation with and without polymer dispersant.

Figure 5:
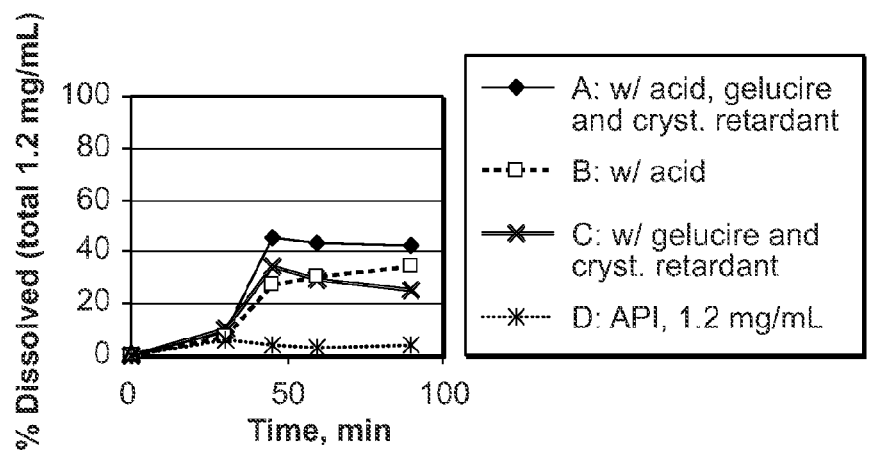
FIG. 5 depicts the results of the 2-step dissolution test performed following Method 3. Dissolution of RX-Drug was tested in a buffer at pH 4.0 for 0-30 minutes and then after transferring to a buffer at pH 6.5 for 30-90 minutes. Both buffers had of 0.9% NaCl. The two-step dissolution with 0.9% NaCl was used to simulate common ion effect.

FIG. 5 depicts the results of the 2-step dissolution test performed following Method 3 described in Table 11 (see above). Dissolution of RX-Drug was tested in a buffer at pH 4.0 for 0-30 minutes and then after transferring to a buffer at pH 6.5 for 30-90 minutes. Both buffers had of 0.9% NaCl. The two-step dissolution with 0.9% NaCl was used to simulate common ion effect. Method 3 is more discriminating and slowed the release of formulation A by 50% due to common ion effect. The dissolution of formulation C with Gelucire and crystallization retardant, on the other hand, increased significantly, but still less than formulation A, which contains acidifier in addition to gelucire and binder.

Figure 6:
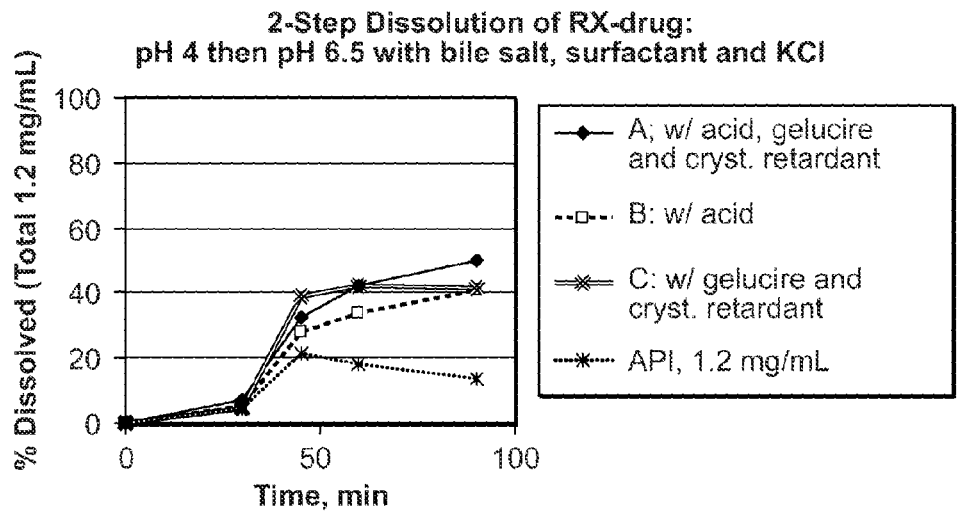
FIG. 6 depicts the results of the 2-step dissolution test performed following Method 4. Dissolution of RX-Drug was tested in a buffer at pH 4 containing NaCl for 0-30 minutes, and then transferred to a buffer at pH 6.5 containing bile salt, surfactant and KCl for 30-90 minutes.

FIG. 6 depicts the results of the 2-step dissolution test performed following Method 4 described in Table 11 (see above). Dissolution of RX-Drug was tested in a buffer at pH 4 containing NaCl for 0-30 minutes, and then transferred to a buffer at pH 6.5 containing bile salt, surfactant and KCl for 30-90 minutes. Method 4 resulted in similar rank order as was observed under Method 3 (FIG. 5; without bile salts and surfactants).

Figure 7:
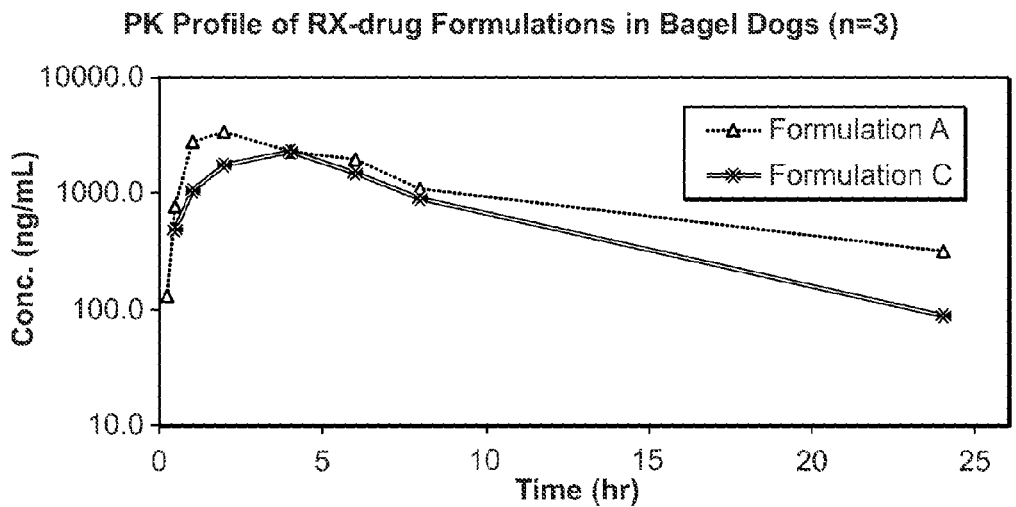
FIG. 7 depicts the PK Profile of RX-drug formulations in beagle dogs (n=3).

FIG. 7 depicts the PK Profile of RX-drug formulations in beagel dogs (n=3). Formula A provided higher exposure than formulation C, which is in agreement with dissolution method C (described in the specification). The Table lists the $C_{max}$, $T_{max}$, $T_{1/2}$, and AUC values.

The 2-Step dissolution using simple buffer with sodium chloride presents an easy-to-use surrogate for the conventional 2-step dissolution system with bile-salts and surfactants. The dissolution in such medium enables the study of super-saturation and common ion effects for formulations of high dose hydrochloride salt drugs with microgram water solubility. The exposure in dog of the model compound is in agreement with the result of dissolution. On the other hand: The simple buffer system without chloride ion did not discriminate the formulations of a drug with a low chloride Ksp. The dissolution with bile salt and surfactant did not provide enough discriminating to rank order the formulations.

The results of study also indicated that: Inclusion of the polymer and surfactant in the formulations effectively improves dissolution and degree of super-saturation of the model compound, a basic salt, in dual pH media. Inclusion of pH modifier in addition to polymer and surfactant improved dissolution/super-saturation and in-vivo exposure of the compound further.

In Vivo Dog Study

Figure 2:
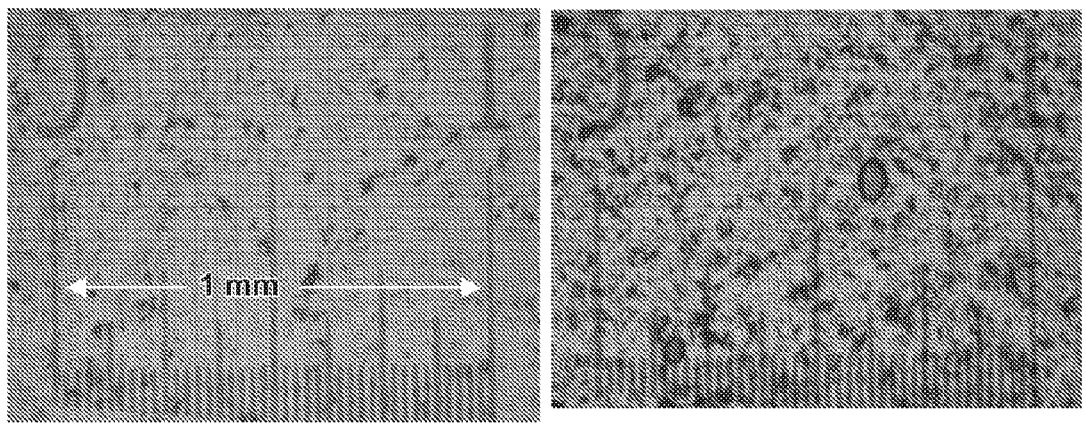
FIG. 2 depicts microscopic images of drug aggregates in the presence of chloride ion related to an in-vivo dog study.

An in-vivo dog study was conducted with beagle dogs (wt=12 kg, n=3). The dogs were dosed orally at 150 mg under fasting conditions. Serial of plasma samples were collected, extracted, and analyzed by LC/MS/MS. $C_{max}$ and AUC were estimated to evaluate the overall exposure from different formulations. Polarized light microscopy of RX-drug (N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide) in water and 0.1N HCl was conducted. The microscopic method was conducted with drug suspended in water, pH 1.2, pH 4.0, and pH 6.5 buffers with or without sodium chloride. Photographs were taken at approximately 30 minutes after preparation. The microscopy indicated that the drug formed aggregates in the presence of chloride ion (left panel). FIG. 2 depicts microscopic images of drug aggregates in the presence of chloride ion.

INCORPORATION BY REFERENCE

The entire disclosure of each of the patent documents, including certificates of correction, patent application documents, scientific articles, governmental reports, websites, and other references referred to herein is incorporated by reference in its entirety for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition comprising an antimicrobial agent, a pharmaceutical carrier, an emulsifier, and a polymeric dissolution aid, wherein said antimicrobial agent is

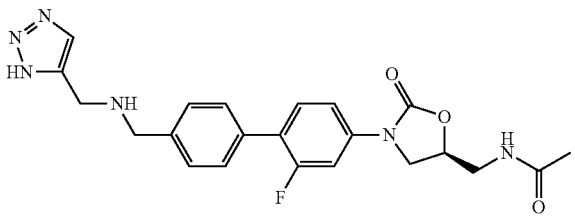 [SMILES: CC(=O)NC[C@H]1CN(c2ccc(-c3ccc(CNCc4cnn[nH]4)cc3)c(F)c2)C(=O)O1]

(S)—N-((3-(4'-((((1H-1,2,3-triazol-5-yl)methyl)amino)methyl)-2-fluoro-[1,1'-biphenyl]-4-yl)-2-oxooxazolidin-5-yl)methyl)acetamide, or a pharmaceutically acceptable salt or tautomer thereof.

2. The pharmaceutical composition according to claim 1 wherein said emulsifier is a polyglycolized glyceride.

3. The pharmaceutical composition according to claim 2 wherein said emulsifier is selected from the group consisting of Labrafil, Labrosol, and Gelucire.

4. The pharmaceutical composition according to claim 3 wherein said emulsifier is selected from the group consisting of Gelucire 50/13, Gelucire 44/14, and mixtures thereof.

5. The pharmaceutical composition according to claim 1 wherein said polymeric dissolution aid is selected from the group consisting of polymers of 1-ethenyl-2-pyrrolidinone; polyamine N-oxide polymers; copolymers of N-vinylpyrrolidone and N-vinylimidazole; polyvinyloxazolidones and polyvinylimidazoles or mixtures thereof.

6. The pharmaceutical composition according to claim 5 wherein said polymeric dissolution aid is a polymer of 1-ethenyl-2-pyrrolidinone.

7. The pharmaceutical composition according to claim 5 wherein said polymeric dissolution aid is polyvinylpyrrolidone.

8. The pharmaceutical composition according to claim 1 further comprising a binder, filler, dispersant or wetting agent, disintegrant, or lubricant.

9. The pharmaceutical composition according to claim 1 further comprising one or more components selected from the group consisting of water, a nonaqueous solvent, a coating, a capsule shell, a colorant, a flavoring, a preservative, an antioxidant, a flavor enhancer, a compression aid, and a surfactant.

10. The pharmaceutical composition according to claim 1 in the form of a tablet.

11. The pharmaceutical composition according to claim 1 in the form of a capsule.

12. A method of treating or reducing the risk of a microbial infection in a patient comprising administering a pharmaceutically effective amount of a pharmaceutical composition according to claim 1.

13. The method of claim 12 wherein the patient is a mammal or a domestic animal.

14. The method according to claim 12 wherein the composition, compared to a control composition, provides at least a 5% improvement in dissolution in a two step dissolution testing system.

15. The method according to claim 14 wherein the two step dissolution system comprises measuring the dissolution in a first step in a simulated gastric environment of about pH 4 for up to 30 minutes followed by measuring the dissolution in a second step in a simulated gastric environment of about pH 5.4 to about 6.5 for up to about 60 minutes.

* * * * *